(12) United States Patent
Oh et al.

(10) Patent No.: US 10,577,609 B2
(45) Date of Patent: Mar. 3, 2020

(54) GLYPICAN-3 SPECIFIC APTAMER AND USE THEREOF

(71) Applicant: POSTECH ACADEMY—INDUSTRY FOUNDATION, Pohang (KR)

(72) Inventors: Eun Ju Oh, Pohang (KR); Jung Hwan Lee, Seoul (KR); Jong-Hoon Lim, Seoul (KR); Jong In Kim, Seoul (KR); Jung Hwan Yoon, Seoul (KR); Sung Ho Ryu, Pohang (KR); Jeong-Hoon Lee, Seoul (KR); Won Jun Kang, Goyang (KR); Seong Hui Jin, Pohang (KR)

(73) Assignees: POSTECH ACADEMY—INDUSTRY FOUNDATION, Pohang-si (KR); SEOUL NATIONAL UNIVERSITY HOSPITAL, Seoul (KR); YONSEI UNIVERSITY, UNIVERSITY—INDUSTRY FOUNDATION (UIF), Seoul (KR)

(*) Notice: Subject to any disclaimer, the term of this patent is extended or adjusted under 35 U.S.C. 154(b) by 0 days.

(21) Appl. No.: 15/450,119

(22) Filed: Mar. 6, 2017

(65) Prior Publication Data

US 2019/0136239 A1 May 9, 2019

(30) Foreign Application Priority Data

Mar. 7, 2016 (KR) .................. 10-2016-0027298
Mar. 6, 2017 (KR) .................. 10-2017-0028326

(51) Int. Cl.
*C12N 15/115* (2010.01)
*C12Q 1/68* (2018.01)
*A61K 31/7088* (2006.01)
*C12Q 1/6886* (2018.01)

(52) U.S. Cl.
CPC ........ *C12N 15/115* (2013.01); *A61K 31/7088* (2013.01); *C12Q 1/6886* (2013.01); *C12N 2310/16* (2013.01); *C12N 2310/3517* (2013.01)

(58) Field of Classification Search
None
See application file for complete search history.

(56) References Cited

U.S. PATENT DOCUMENTS

2010/0055695 A1* 3/2010 Zichi .................. C12N 15/1048
435/6.12
2015/0285806 A1* 10/2015 Ohtomo ........... G01N 33/57438
435/7.92

FOREIGN PATENT DOCUMENTS

KR 10-2014-0004552 1/2014

OTHER PUBLICATIONS

Thai Quang Nguyen et al., "In vitro Selection of ssDNA Aptamers to Glypican-3 (GPC3) Protein for Use in Diagnosis of HCC", The Korean Society for Biotechnology and Bioengineering, Oct. 2013, p. 336, KSBB, Abstracts of Current Biotechnology and Bioengineering(XXXII) (see the red box part).
Mingqian Feng et al., "Glypican-3 antibodies: a new therapeutic target for liver cancer", FEBS Lett., Jan. 21, 2014, vol. 588, No. 2, pp. 377-382.
Yun Bin Lee et al., "Glypican-3 Aptamer Has Potential as a New Targeted Therapy for Hepatocellular Carcinom", AASLD the Liver Meeting, Poster Abstract, Nov. 11, 2016.

* cited by examiner

*Primary Examiner* — Tracy Vivlemore
(74) *Attorney, Agent, or Firm* — Lex IP Meister, PLLC

(57) ABSTRACT

The present invention relates to a DNA aptamer specifically binding to a hepatocellular carcinoma-related Glypican-3 (GPC3) protein, treatment of cancers related to the Glypican-3 protein using the same, a composition for inhibiting a cancer and a composition for diagnosing a cancer comprising the same as an active ingredient.

11 Claims, 25 Drawing Sheets
Specification includes a Sequence Listing.

Fig. 2a

Sequence Analysis Report (Sorted)
s003-H10

86.67% (39/45) Multi-Copy

[1] s003-H10001-T7_A07  Count: 2  4.44%  GTTGACTTGATTGGGACTTGTTCAGTAACGCAGCCTTGAC  [1, 21]
(SEQ ID NO:49)

[10] s003-H10010-T7_B08  Count: 15  33.33%  TTTCCGCTGTATTTAGCAGTGAGCGTTTATTCGCCTCAAA  [10, 15, 16, 17, 24,
(SEQ ID NO:50)                                                                        31, 34, 35, 36, 37,
                                                                                      39, 40, 43, 44, 46]

[11] s003-H10011-T7_C08  Count: 5  11.11%  TATGATTGGGCAGATTAAACTTCCGCAGCAGTTTTCCCGG  [3, 5, 7, 11, 30]
(SEQ ID NO:51)

[12] s003-H10012-T7_D08  Count: 3  6.67%  CGCAGTCCGTTGACTTATTTGCACCCGTGTGATTGTTCAGT  [12, 13, 18]
(SEQ ID NO:52)

[19] s003-H10019-T7_C09  Count: 3  6.67%  GCGTTGACTTATCATCCCCCAGTCGGCTTGCAGGCCGGCT  [8, 19, 23]
(SEQ ID NO:53)

[22] s003-H10022-T7_F09  Count: 7  15.56%  CTCGTTGACTTATCTCACCTTCAGTAGGGTCTGAGCGTCG  [9, 22, 25, 29, 41,
(SEQ ID NO:54)                                                                          42, 45]

[26] s003-H10026-T7_B10  Count: 2  4.44%  GTAAATAGTGTGTGATTGTGTAATCAGTTTACAGACGGG  [26, 32]
(SEQ ID NO:55)

[4] s003-H10004-T7_D07  Count: 2  4.44%  TCGGCTGGTCTGCGTGTGTTGTCGGCATGTAGATCTCGCG  [4, 27]
(SEQ ID NO:56)

Fig. 2b

95.56% (43/45) Families
1.[Pattern_1]                          TTTATTC (SEQ ID NO:57)
[38]  1  2.22%    AGTGCTCTATTATGCCGGGCTATTTATTCCGGGGCGGTT (SEQ ID NO:58)
[10]  15  33.33%  TTTCCGCTGTATTTAGCAGTGAGCGTTTATTCGCCTCAAA (SEQ ID NO:59)
2.[Pattern_4]                          CGTTGACTTAT (SEQ ID NO:60)
[22]  7  15.56%   CTGTTGACTTATTCATTCAGTAGGGTCTGAGCGTCG (SEQ ID NO:61)
[19]  3  6.67%    GCTTGACTTATTATCCCCCAGTCGGCTTGCAGGCCGGCT (SEQ ID NO:62)
[ 6]  1  2.22%    TCAGCTTCCGTTGACTTATATCTTCAGTGAAGCCCTCT (SEQ ID NO:63)
[12]  3  6.67%    CGCAGTCCGTTGACTTATTTGCACCGTGTGATTGTTCAGT (SEQ ID NO:64)
3.[Pattern_8]                          TTCAGTA (SEQ ID NO:65)
[ 2]  1  2.22%    GGGGAGTTAACGCGTTGAATTATGTCCCTTCAGTCGGCAC (SEQ ID NO:66)
[14]  1  2.22%    GGGAAGTGAATGCGTTGAATTATGTCCCTTCAGTCATCAC (SEQ ID NO:67)
[22]  7  15.56%   CTGTTGACTTATTCATTCAGTAGGGTCTGAGCGTCG (SEQ ID NO:68)
[ 6]  1  2.22%    TCAGCTTCCGTTGACTTATATCTTCAGTGAAGCCCTCT (SEQ ID NO:69)
[ 1]  2  4.44%    GTTGACTGATTTGGACTTGTTCAGTAACGCAGCCTTGAC (SEQ ID NO:70)
4.[Pattern_6]                          CCTTCAGT (SEQ ID NO:71)
[ 2]  1  2.22%    GGGGAGTTAACGCGTTGAATTATGTCCCTTCAGTCGGCAC (SEQ ID NO:72)
[14]  1  2.22%    GGGAAGTGAATGCGTTGAATTATGTCCCTTCAGTCATCAC (SEQ ID NO:73)
[22]  7  15.56%   CTGTTGACTTATTCATTCAGTAGGGTCTGAGCGTCG (SEQ ID NO:74)
[ 6]  1  2.22%    TCAGCTTCCGTTGACTTATATCTTCAGTGAAGCCCTCT (SEQ ID NO:75)
5.[Pattern_7]     CGTTGACTTATC (SEQ ID NO:76)
[22]  7  15.56%   CTGTTGACTTATTCATTCAGTAGGGTCTGAGCGTCG (SEQ ID NO:77)
[19]  3  6.67%    GCTTGACTTATCATCCCCCAGTCGGCTTGCAGGCCGGCT (SEQ ID NO:78)
6.[Pattern_3]     TGATTTGG (SEQ ID NO:79)
[11]  5  11.11%   TGATTTGGCAGATTAAACTTCCGCAGCAGTTTTCCCGG (SEQ ID NO:80)
[ 1]  2  4.44%    GTTGACTGATTTGGACTTGTTCAGTAACGCAGCCTTGAC (SEQ ID NO:81)
7.[Pattern_12]                         TGATTTC (SEQ ID NO:82)
[11]  5  11.11%   TGATTTCGCAGATTAAACTTCCGCAGCAGTTTTCCCGG (SEQ ID NO:83)
[26]  2  4.44%    GTAAATAGTGATTTCTGTAATCAGTTTACAGACGGG (SEQ ID NO:84)

8.[Pattern_2]                          GATTAAA (SEQ ID NO:85)
[11]  5  11.11%   TGATTTCGCAGATTAAACTTCCGCAGCAGTTTTCCCGG (SEQ ID NO:86)
[33]  1  2.22%    GCTTCTTCGATTGAATTTAAGATATGCGTCCTCAGACACA (SEQ ID NO:87)
[20]  1  2.22%    TATGTTTTGGAGGATTAAATCCCGCGATTTTCAGAGTGCCCC (SEQ ID NO:88)

Fig. 2c

Sequence Analysis Report (Sorted)

S033-C1 GPC3 6R Bz 94.00% (47/50) Multi-Copy

| | | | | |
|---|---|---|---|---|
| [1] S033-C1-01-M13-20R_A01 Count: 16 | 32.00% | GTAATAAATAGTGACTGATTTTGTGTTCCGTTACACCAA (SEQ ID NO:89) | [1, 3, 4, 7, 18, 20, 21, 22, 23, 27, 28, 29, 39, 40, 41, 48] |
| [10] S033-C1-10-M13-20R_B0 Count: 5 | 10.00% | GTGTATGCGGTTGGGGCAAGCTCCGTTACGTGCTATGGT (SEQ ID NO:90) | [10, 15, 19, 32, 34] |
| [11] S033-C1-11-M13-20R_C0 Count: 5 | 10.00% | ATGTGATAAATAGTAATTGATTTTGTACTCAGTTACATA (SEQ ID NO:91) | [11, 31, 33, 35, 36] |
| [12] S033-C1-12-M13-20R_D0 Count: 10 | 20.00% | GATCATAAATAGTTTCTGATTTTGTAGTCCGTTACGAGA (SEQ ID NO:92) | [5, 8, 12, 13, 14, 24, 38, 44, 45, 47] |
| [17] S033-C1-17-M13-20R_A0 Count: 2 | 4.00% | GGCACCTCCCCTTGACTTATATCCACCTTCAGTGGGTGC (SEQ ID NO:93) | [17, 26] |
| [2] S033-C1-02-M13-20R_B0 Count: 4 | 8.00% | ACGTGCTTTTTAATGTACCGGGTTTGTCCGGGCAGCGA (SEQ ID NO:94) | [2, 42, 49, 50] |
| [25] S033-C1-25-M13-20R_A0 Count: 3 | 6.00% | TACGTGCCGTTGACTTATATCCCTCAGTGTCCTTCCTC (SEQ ID NO:95) | [6, 9, 25] |
| [37] S033-C1-37-M13-20R_E0 Count: 2 | 4.00% | CGTCAGAGCTGGTTGCGGTGCCCGGTATTTGCTCCGGCGCC (SEQ ID NO:96) | [37, 43] |

Fig. 2d

Sequence Analysis Report (Sorted)
S033-C1 GPC3 6R Bz
88.00% (44/50) Families 1. [Pattern_4]      ATAAATAGT (SEQ ID NO:97)
   [12]  10     20.00%   GATCATAAATAGTT........AGTCCGTTTACGAGA (SEQ ID NO:98)
   [ 1]  16     32.00%   GTAATAAATAGTGACTGATTTGTGTTCCGTTTACACCAA (SEQ ID NO:99)
   [11]  5  10.00%   ATGTGATAAATAGTAATTGA.....ACTCAGTTTACATA (SEQ ID NO:100)

2. [Pattern_2]      TGATTTTGTA (SEQ ID NO:101)
   [12]  10     20.00%   GATCATAAATAGTT........AGTCCGTTTACGAGA (SEQ ID NO:102)
   [46]  1  2.00%         TAAATAGTGTCT.......ATCGTTTATCGCTAGAAGCT (SEQ ID NO:103)
   [ 1]  16     32.00%   GTAATAAATAGTGACTGATTTGTGTTCCGTTTACACCAA (SEQ ID NO:104)
   [11]  5  10.00%   ATGTGATAAATAGTAATTGA.....ACTCAGTTTACATA (SEQ ID NO:105)

3. [Pattern_5]      CTGATTTTGT (SEQ ID NO:106)
   [12]  10     20.00%   GATCATAAATAGTT........AGTCCGTTTACGAGA (SEQ ID NO:107)
   [ 1]  16     32.00%   GTAATAAATAGTGACTGATTTGTGTTCCGTTTACACCAA (SEQ ID NO:108)

4. [Pattern_9]      TAAATAGTG (SEQ ID NO:109)
   [46]  1  2.00%      TAAATAGTGTCT.......ATCGTTTATCGCTAGAAGCT (SEQ ID NO:110)
   [ 1]  16     32.00%   GTAATAAATAGTGACTGATTTGTGTTCCGTTTACACCAA (SEQ ID NO:111)

5. [Pattern_3]      TTTGTACT (SEQ ID NO:112)
   [12]  10     20.00%   GATCATAAATAGTT........AGTCCGTTTACGAGA (SEQ ID NO:113)
   [11]  5  10.00%   ATGTGATAAATAGTAATTGA.....ACTCAGTTTACATA (SEQ ID NO:114)
   [16]  1  2.00%   ACGAAAATCTATACTTTCAAG..........ACTAAATCCCG (SEQ ID NO:115)

6. [Pattern_6]      ........ (SEQ ID NO:116)
   [12]  10     20.00%   GATCATAAATAGTT........AGTCCGTTTACGAGA (SEQ ID NO:117)
   [46]  1  2.00%      TAAATAGTGTCT.......ATCGTTTATCGCTAGAAGCT (SEQ ID NO:118)

7. [Pattern_8]      TGACTTATCC (SEQ ID NO:119)
   [30]  1  2.00%   ATGGTGGCTAACTTGG................... (SEQ ID NO:120)
   [25]  3  6.00%         TACGTG.....................CTCCTTCCCTC (SEQ ID NO:121)
   [17]  2  4.00%      GGCACCTCCCC...........ACCTTCAGTGGGGTGC (SEQ ID NO:122)

Fig. 2e

Sequence Analysis Report (Sorted)
S033-D1 GPC3 6R Nap

42.86% (21/49) Multi-Copy

[1] S033-D1-01-M13-20R_A07  Count 2   4.08%  GATAACAAGTGTGTGAATTTATCACGTGAAACTAGCCGTTG [1, 50]
(SEQ ID NO:123)

[10] S033-D1-10-M13-20R_B08  Count 7  14.29%  TACAAGATGTGAATTTATCCCGTGAGTGGCATCGTGACC [5, 10, 13, 15, 33, 40, 43]
(SEQ ID NO:124)

[12] S033-D1-12-M13-20R_D08  Count 2   4.08%  GCATATGAGGGTAGGCTAGCCATCTTTGGGGCAGCAGGA [12, 30]
(SEQ ID NO:125)

[19] S033-D1-19-M13-20R_C08  Count 6  12.24%  TTTGGGGTGGTAGGACACGGTGAATAAAGATCTGGCCCGC [4, 9, 19, 21, 36, 39]
(SEQ ID NO:126)

[32] S033-D1-32-M13-20R_H10  Count 2   4.08%  CAATGTAAGTGCATTAAATTTTTGCCAAGGCCTCAGCTGC [32, 49]
(SEQ ID NO:127)

[7] S033-D1-07-M13-20R_007  Count 2   4.08%  TCAAGATGTGAATTTATCACCGTGGGGCGAAGGACCTGTG [7, 35]
(SEQ ID NO:128)

Fig. 2f

Sequence Analysis Report (Sorted)
S033-D1 GPC3 6R Nap
75.51% (37/49) Families

```
1.[Pattern_1]                        TTTGAATTTATC (SEQ ID NO:129)
 [ 2]  1  2.04%   AAACAGGATGGTCAAGATGTGAATTTATCCCTGTGTCC (SEQ ID NO:130)
 [10]  7 14.29%          TA                         AGTGGCATCGTGACC (SEQ ID NO:131)
 [ 3]  1  2.04%   TAGGGGCGCTGTCAAGATGTGAAT      TGATATCG (SEQ ID NO:132)
 [23]  1  2.04%          AACGT                    TAC        GG (SEQ ID NO:133)
 [ 7]  2  4.08%           TCAAGATGTGAATTTATC   GGGCGAAGGACCTGTG (SEQ ID NO:134)
 [24]  1  2.04%           TC                      AAGGCTGCAGCCCCTA (SEQ ID NO:135)
 [ 1]  2  4.08%   GATAACAAGCTGTGAAT          TGAAACTAGCCGTTG (SEQ ID NO:136)

2.[Pattern_32]                              TTTATCCC (SEQ ID NO:137)
 [ 2]  1  2.04%   AAACAGGATGGTCAAGATGTGAATTTATCCCTGTGTCC (SEQ ID NO:138)
 [10]  7 14.29%          TA                         AGTGGCATCGTGACC (SEQ ID NO:139)
 [ 3]  1  2.04%   TAGGGGCGCTGTCAAGATGTGAAT      TGATATCG (SEQ ID NO:140)
 [ 1]  2  4.08%   GATAACAAGCTGTGAAT          TGAAACTAGCCGTTG (SEQ ID NO:141)
 [28]  1  2.04%   CCGTACATTTGTTGAAGAAGCGC      ATCCTGTGC (SEQ ID NO:142)

3.[Pattern_2]                        CAAGATGTGAATTTATC (SEQ ID NO:143)
 [ 2]  1  2.04%   AAACAGGATGGTCAAGATGTGAATTTATCCCTGTGTCC (SEQ ID NO:144)
 [10]  7 14.29%          TA                         AGTGGCATCGTGACC (SEQ ID NO:145)
 [ 3]  1  2.04%   TAGGGGCGCTGTCAAGATGTGAAT      TGATATCG (SEQ ID NO:146)
 [ 7]  2  4.08%           TCAAGATGTGAATTTATC   GGGCGAAGGACCTGTG (SEQ ID NO:147)

4.[Pattern_6]                        AGTGAAGT (SEQ ID NO:148)
 [44]  1  2.04%   AGAAGTTGGAGGCAATGTAAGT  CATTAATTTTTGCCGA (SEQ ID NO:149)
 [48]  1  2.04%   TACAACAGAAGGCGC GGGCATGTAAGT GTTAATTTTT (SEQ ID NO:150)
 [38]  1  2.04%   AGATGTCCTGGAGGCGGAATGTAAGT ATTAATTTTTCG (SEQ ID NO:151)
 [17]  1  2.04%   ATATGTGGTGCTGAGGGAATGTAAGT  ACCATTTTT (SEQ ID NO:152)
 [29]  1  2.04%            GGGAATGTAAGTGGTTACTTTTTCACGAGAGTGGACT (SEQ ID NO:153)
 [14]  1  2.04%            CAATGAAGT GGTTAATTTTTGCATGTGGTGCGAGTAA (SEQ ID NO:154)
 [47]  1  2.04%       ACAATGTAAGTGA  GATTTTTGCCAACGGACATGGTG (SEQ ID NO:155)
 [32]  2  4.08%           CA           AATTTTTGCCAAGGCCTCAGCTGC (SEQ ID NO:156)

5.[Pattern_4]                        AATGTAAGT (SEQ ID NO:157)
 [44]  1  2.04%   AGAAGTTGGAGCAATGTAAGT  CATTAATTTTTGCCGA (SEQ ID NO:158)
 [46]  1  2.04%       AACGCAATGTAAGTTGGTTAATTTTTGCGTA      G (SEQ ID NO:159)
 [38]  1  2.04%   AGATGTCCTGGAGGCGGAATGTAAGT ATTAATTTTTCG (SEQ ID NO:160)
 [17]  1  2.04%   ATATGTGGTGCTGAGGGAATGTAAGT  ACCATTTTT (SEQ ID NO:161)
 [29]  1  2.04%            GGGAATGTAAGTGGTTACTTTTTCACGAGAGTGGACT (SEQ ID NO:162)
 [14]  1  2.04%            CAATGAAGT GGTTAATTTTTGCATGTGGTGCGAGTAA (SEQ ID NO:163)
 [47]  1  2.04%       ACAATGTAAGTGA  GATTTTTGCCAACGGACATGGTG (SEQ ID NO:164)
 [32]  2  4.08%           CA           AATTTTTGCCAAGGCCTCAGCTGC (SEQ ID NO:165)
```

Fig. 3a
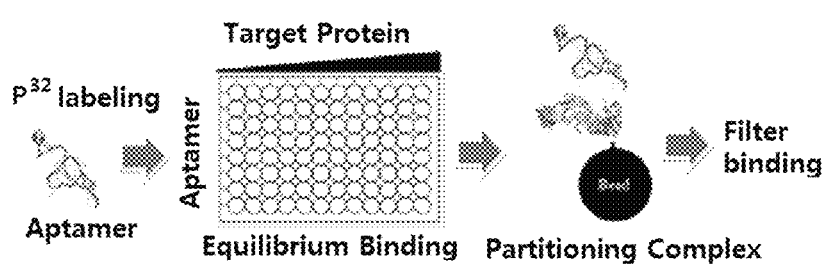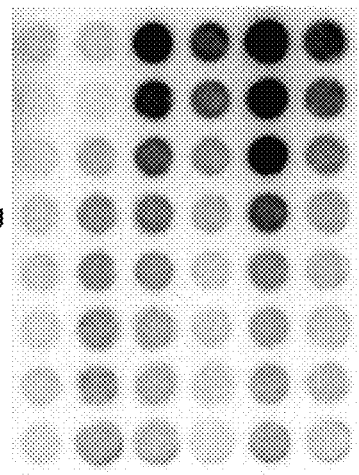
Fig. 3b
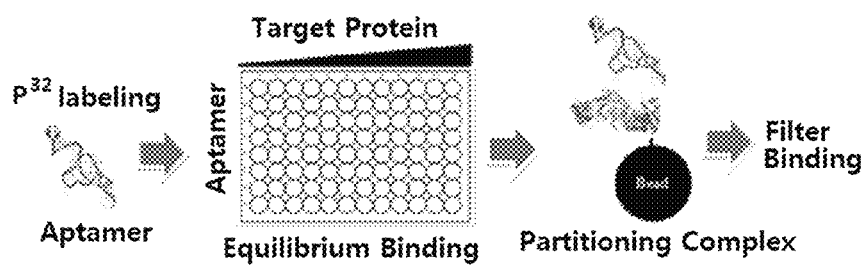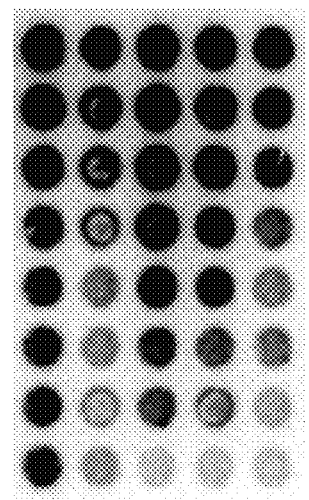

| | #29 | #25 | #24 | #17 | #11 |
|---|---|---|---|---|---|
| Bmax | 0.09 | 0.09 | 0.12 | 0.11 | 0.05 |
| Kd(nM) | 4.25 | 2.35 | 0.19 | 0.21 | 1.36 |

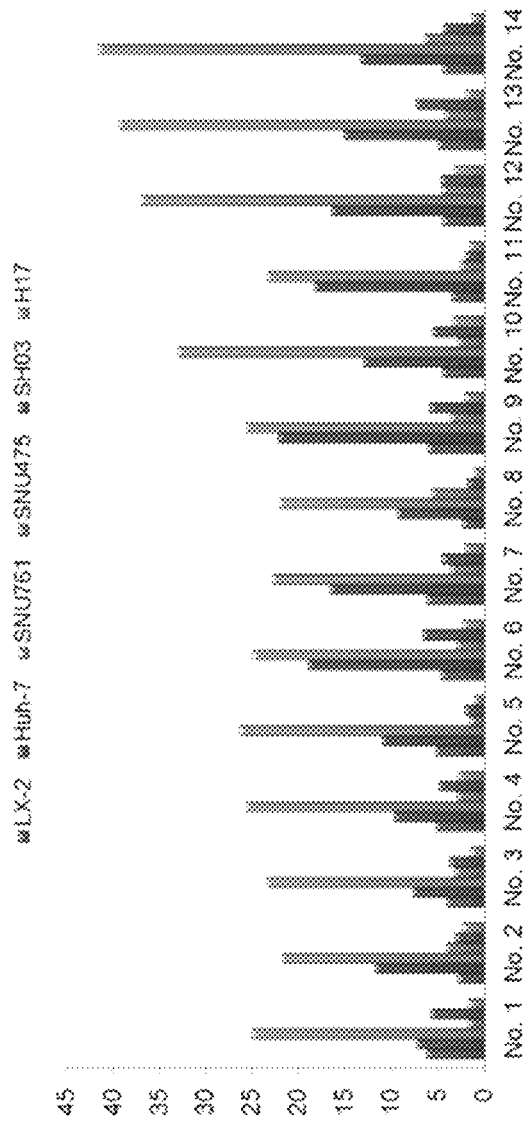

[Fig. 8]
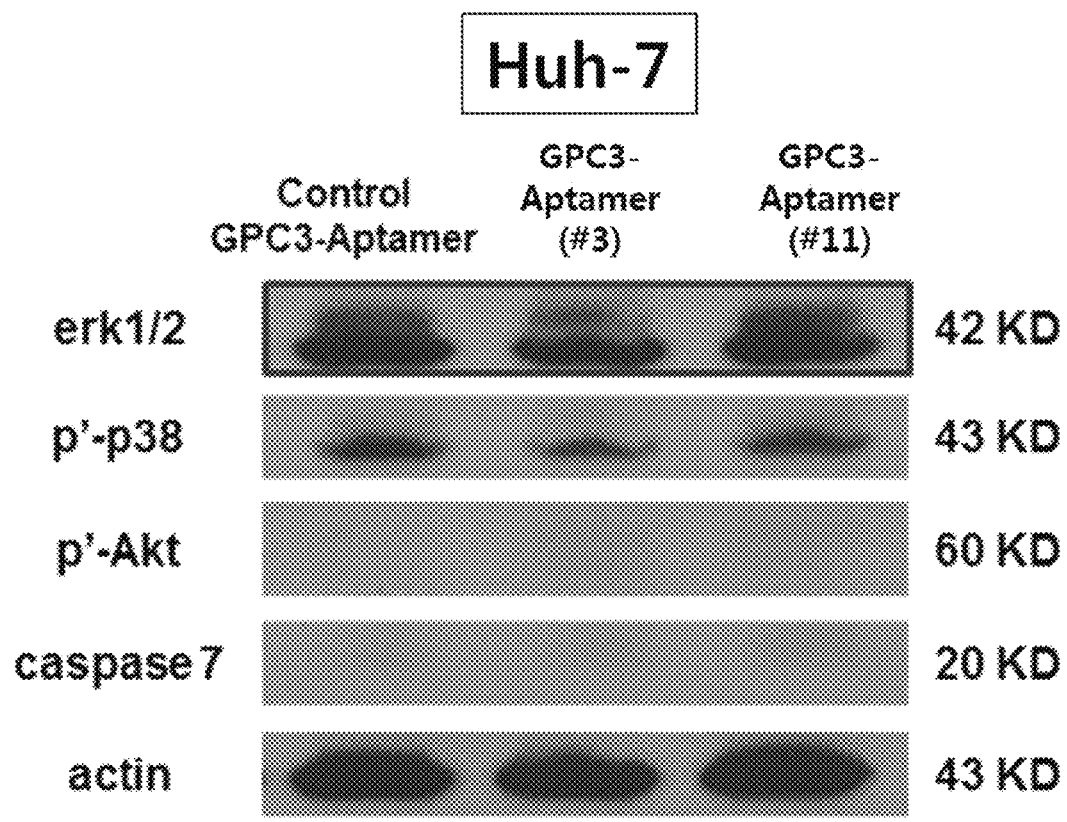

[Fig. 9]
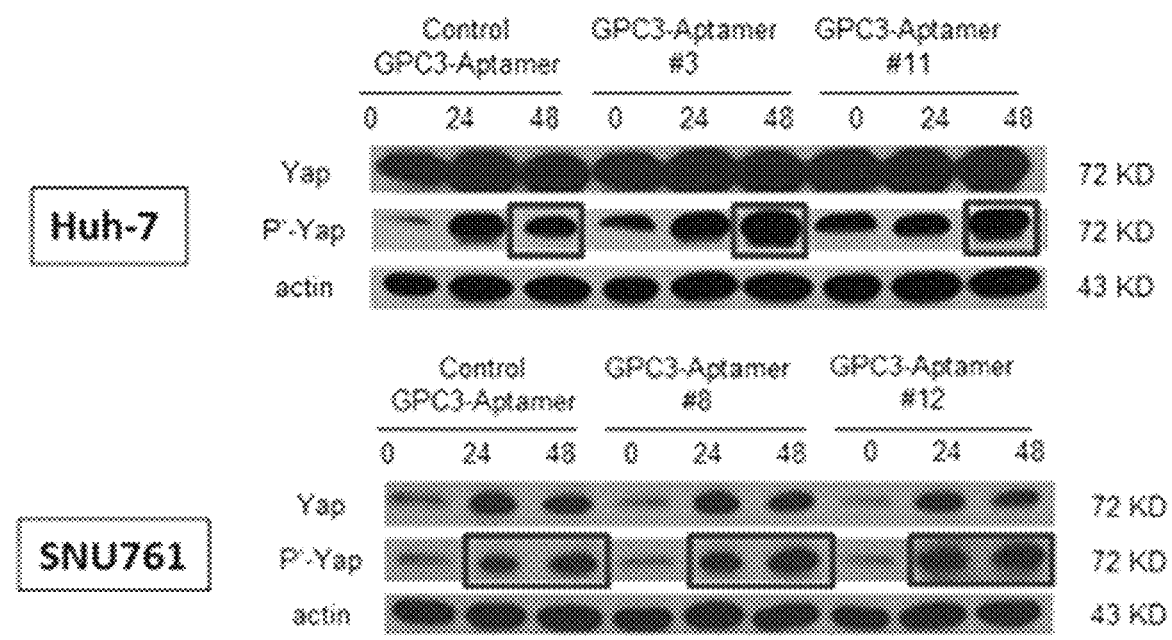

[Fig. 10]
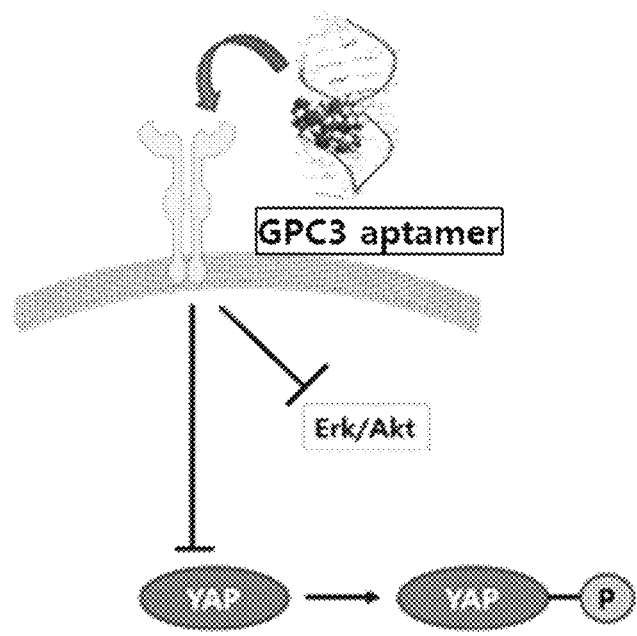

[Fig. 11]
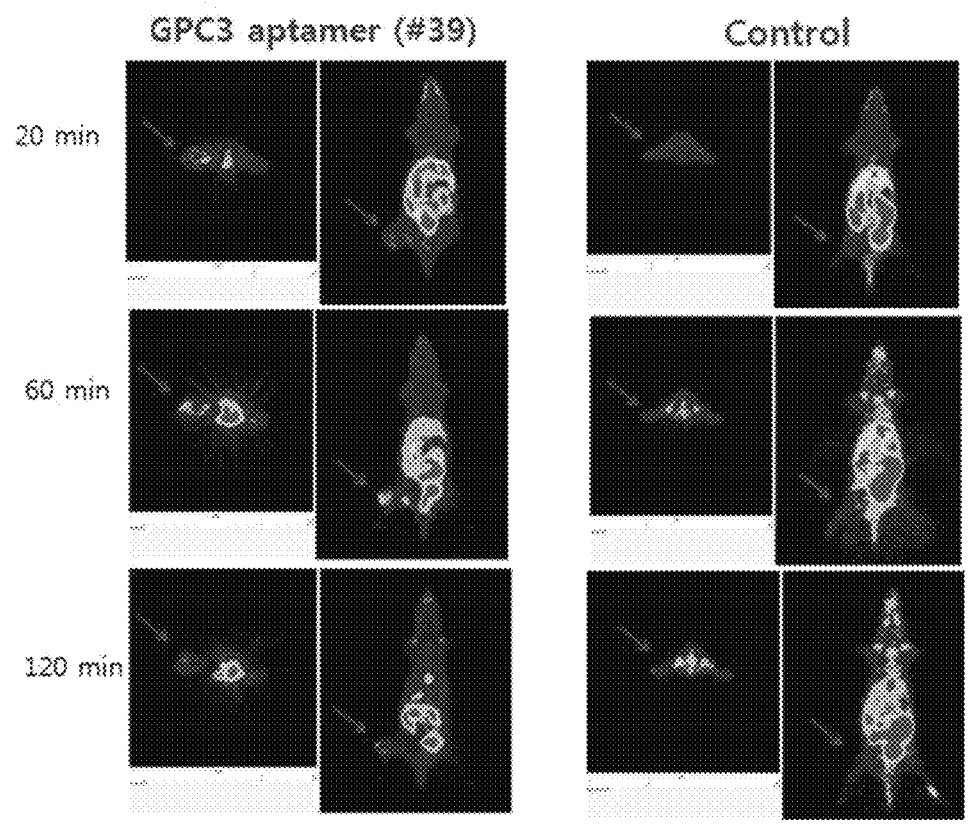

[Fig. 12]
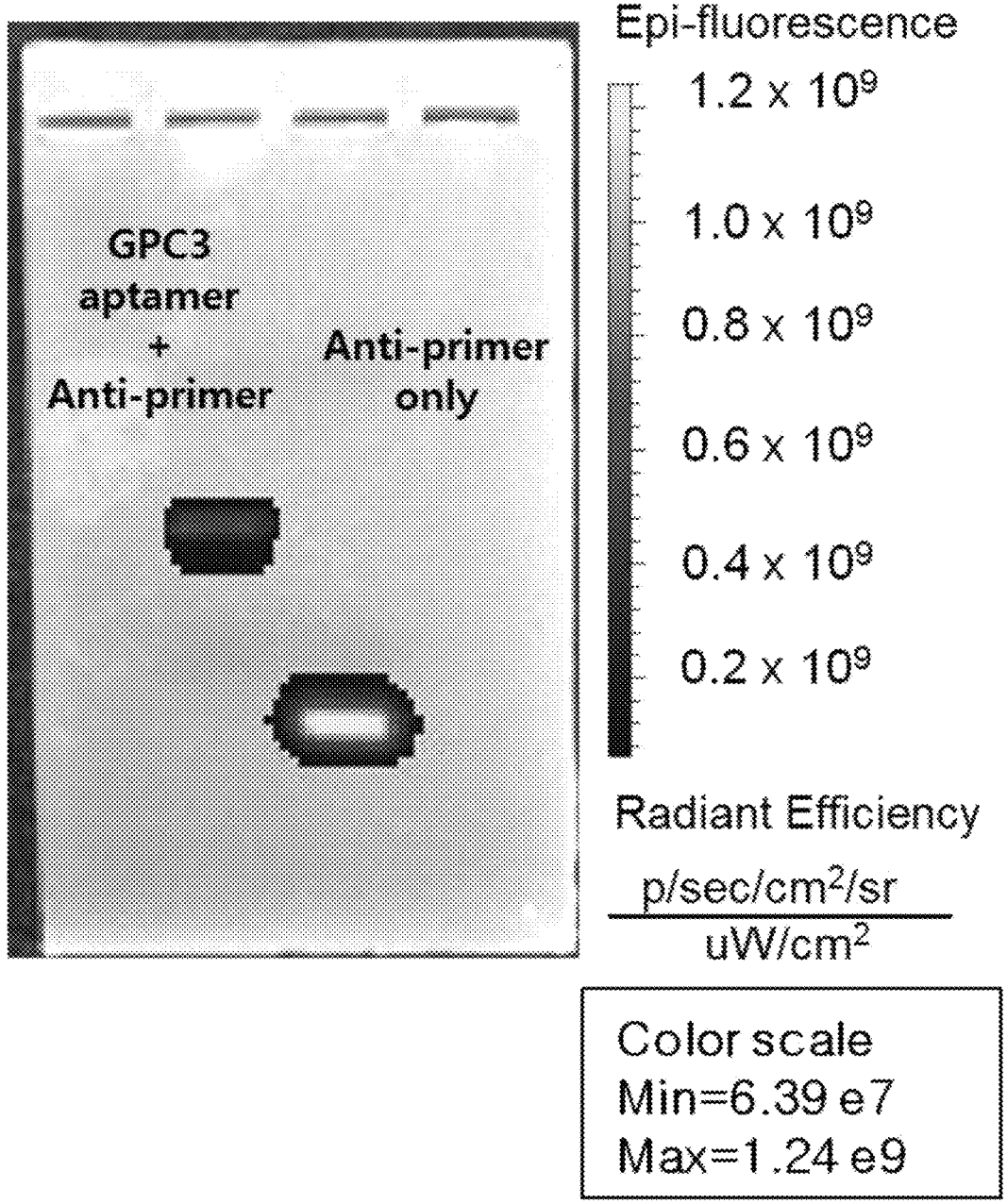

[Fig. 13a]
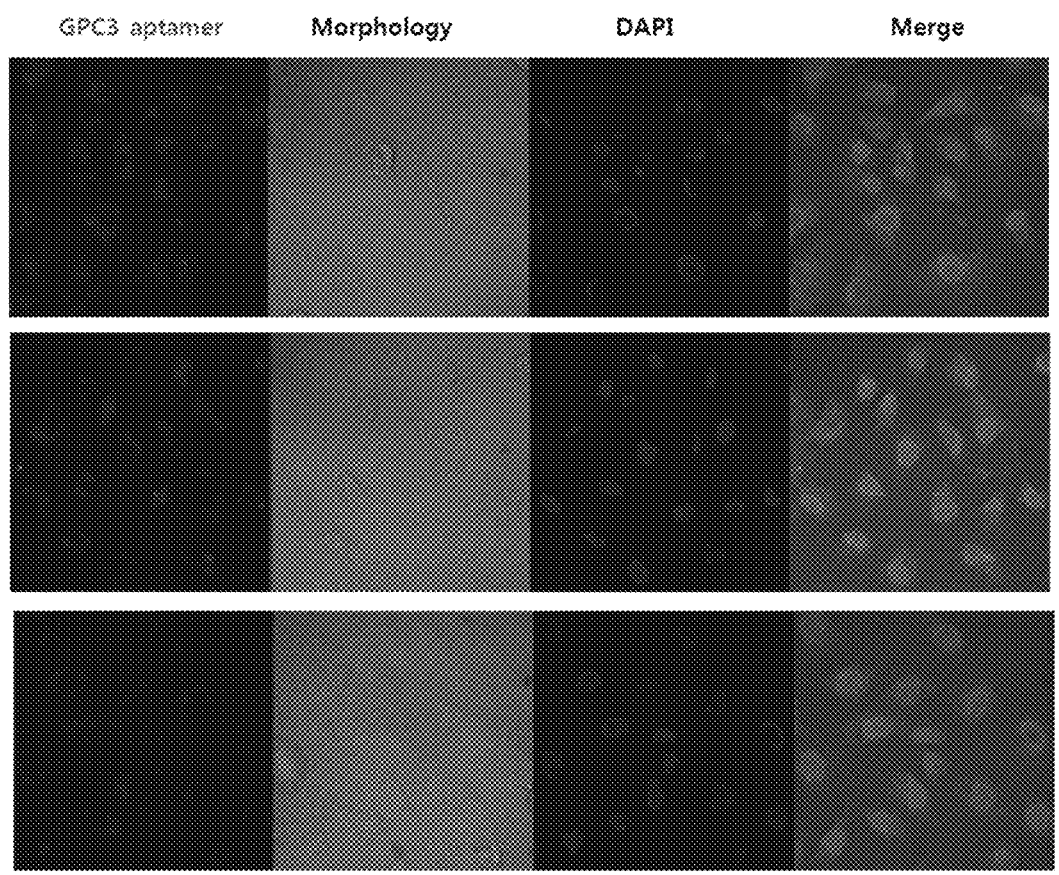

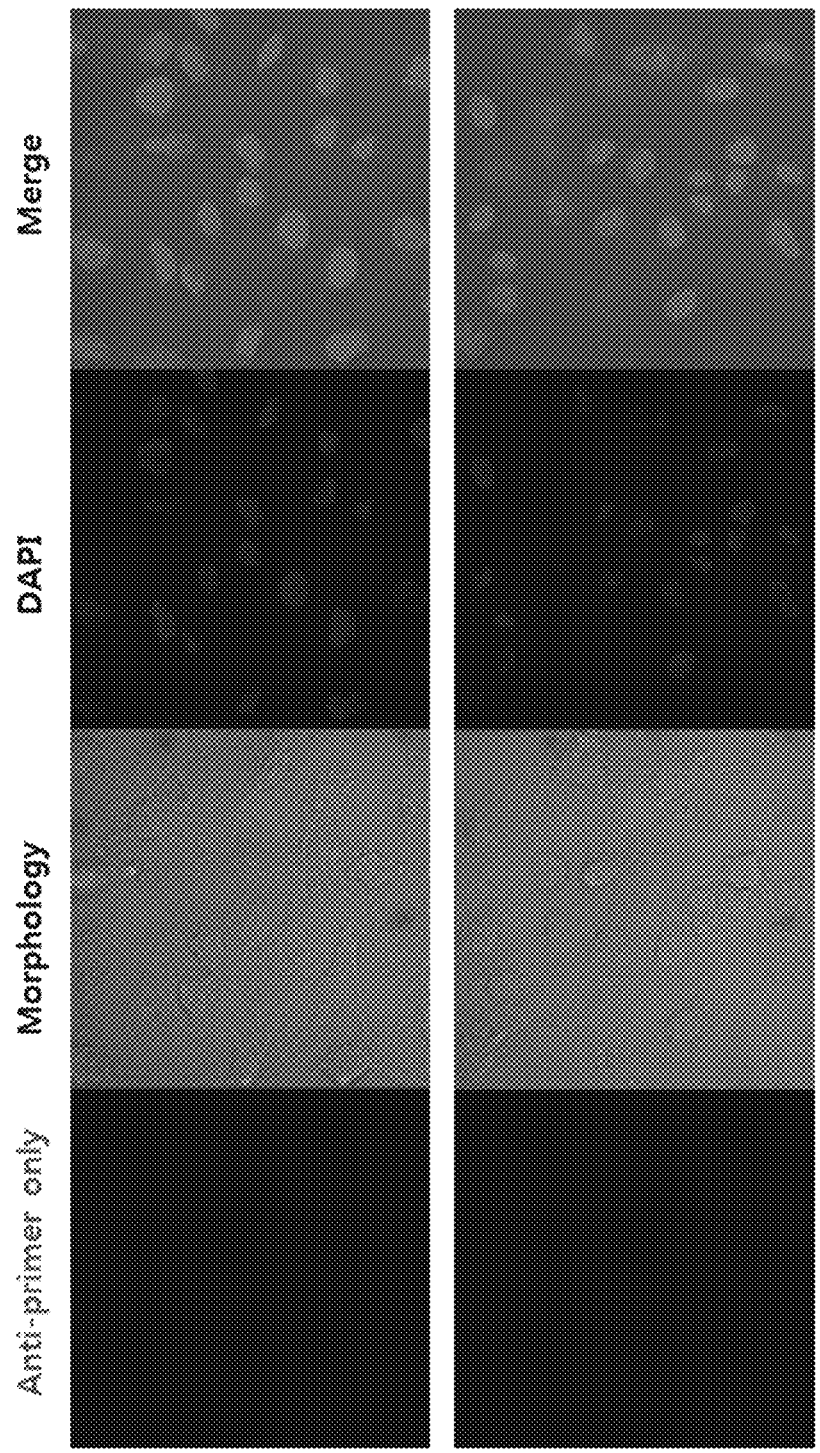
[Fig. 13b]

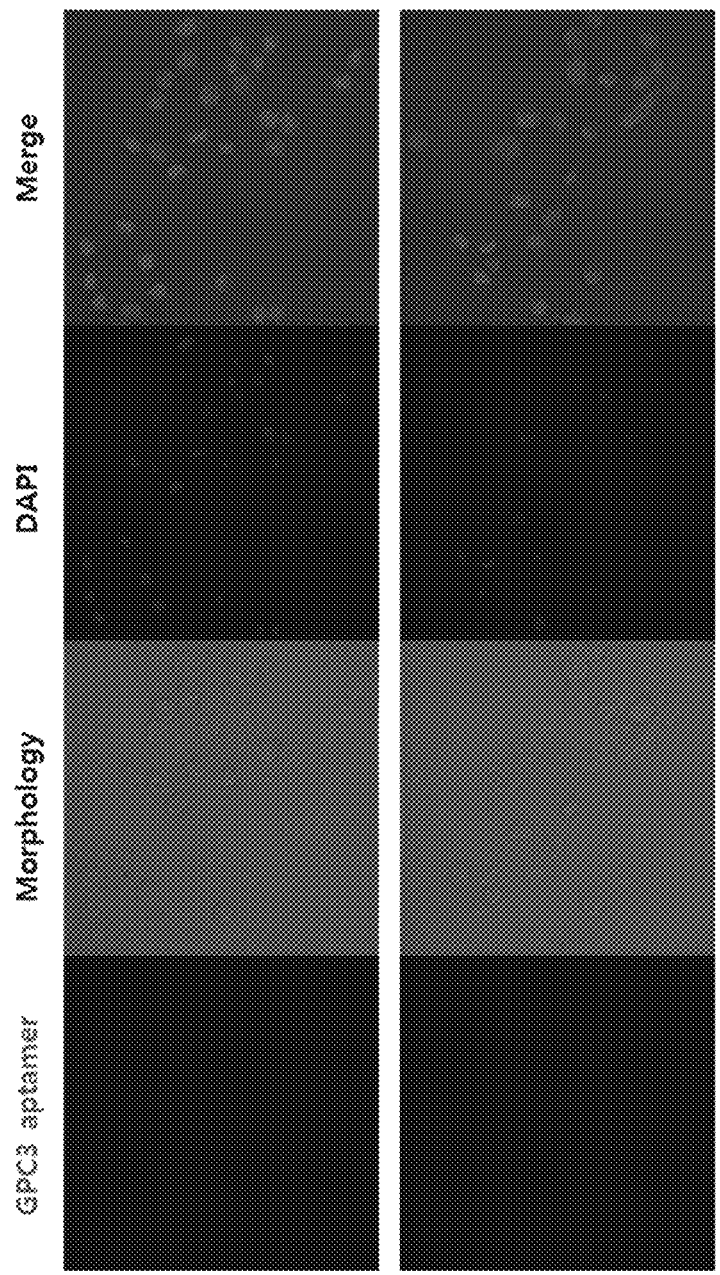
[Fig. 14a]

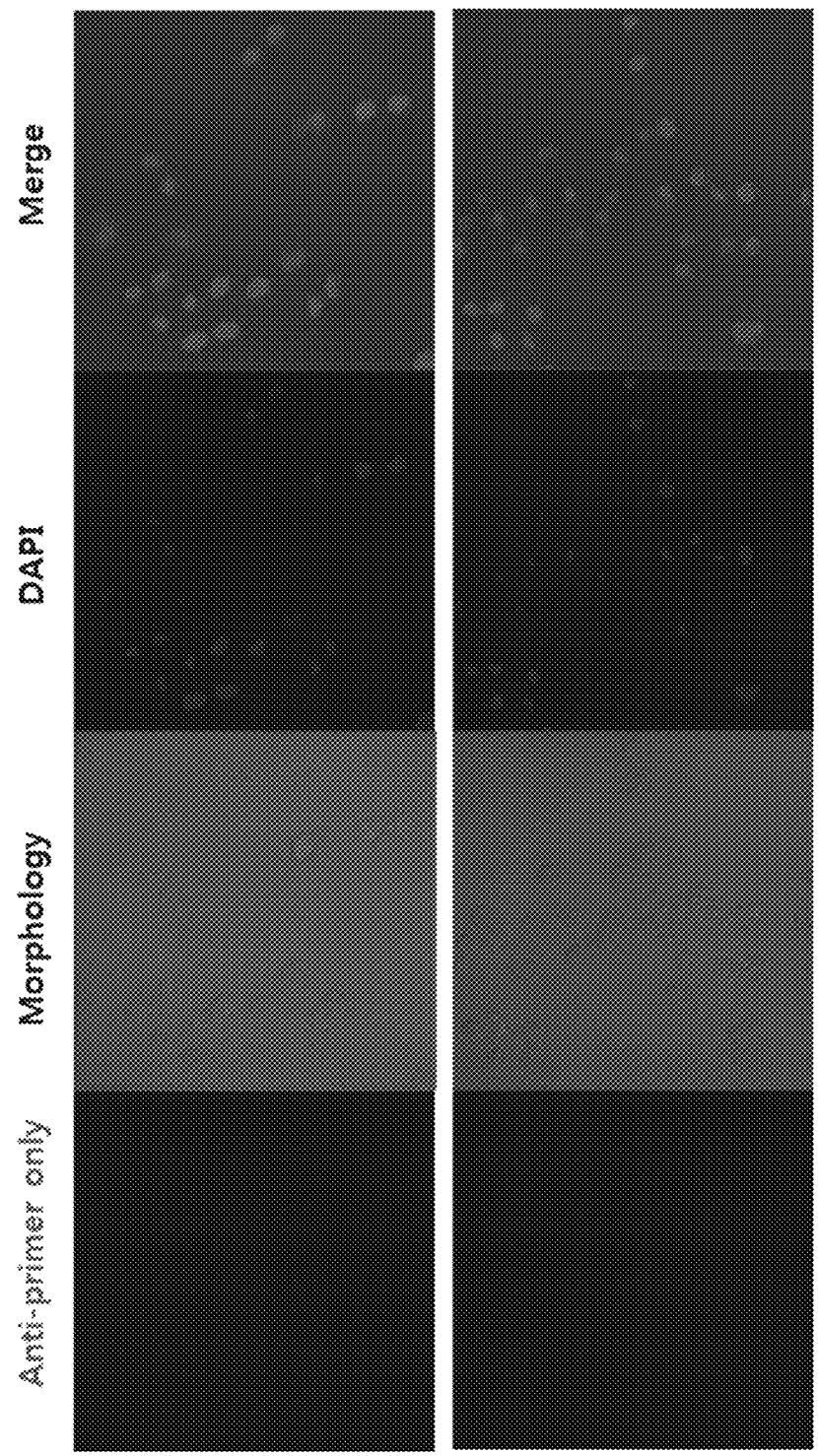
[Fig. 14b]

[Fig. 15]
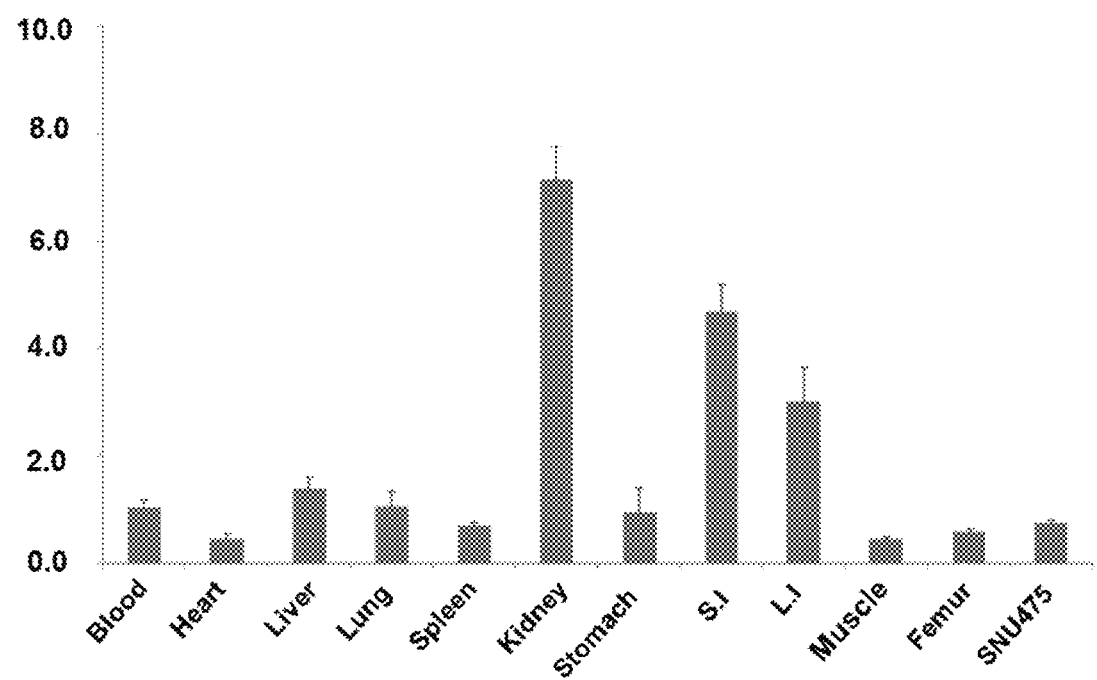

SEQUENCE LISTING

```
<160> NUMBER OF SEQ ID NOS: 167

<210> SEQ ID NO 1
<211> LENGTH: 40
<212> TYPE: DNA
<213> ORGANISM: Artificial Sequence
<220> FEATURE:
<223> OTHER INFORMATION: Synthetic (s003-H10010-T7_B08)
<220> FEATURE:
<221> NAME/KEY: misc_feature
<222> LOCATION: (1)..(3)
<223> OTHER INFORMATION: a base that a benzyl group is introduced to
      5-position of pyrimidine group of deoxyuridine (BzdU)
<220> FEATURE:
<221> NAME/KEY: misc_feature
<222> LOCATION: (8)
<223> OTHER INFORMATION: a base that a benzyl group is introduced to
      5-position of pyrimidine group of deoxyuridine (BzdU)
<220> FEATURE:
<221> NAME/KEY: misc_feature
<222> LOCATION: (10)
<223> OTHER INFORMATION: a base that a benzyl group is introduced to
      5-position of pyrimidine group of deoxyuridine (BzdU)
<220> FEATURE:
<221> NAME/KEY: misc_feature
<222> LOCATION: (12)..(14)
<223> OTHER INFORMATION: a base that a benzyl group is introduced to
      5-position of pyrimidine group of deoxyuridine (BzdU)
<220> FEATURE:
<221> NAME/KEY: misc_feature
<222> LOCATION: (20)
<223> OTHER INFORMATION: a base that a benzyl group is introduced to
      5-position of pyrimidine group of deoxyuridine (BzdU)
<220> FEATURE:
<221> NAME/KEY: misc_feature
<222> LOCATION: (26)..(28)
<223> OTHER INFORMATION: a base that a benzyl group is introduced to
      5-position of pyrimidine group of deoxyuridine (BzdU)
<220> FEATURE:
<221> NAME/KEY: misc_feature
<222> LOCATION: (30)..(31)
<223> OTHER INFORMATION: a base that a benzyl group is introduced to
      5-position of pyrimidine group of deoxyuridine (BzdU)
<220> FEATURE:
<221> NAME/KEY: misc_feature
```

<222> LOCATION: (36)
<223> OTHER INFORMATION: a base that a benzyl group is introduced to
      5-position of pyrimidine group of deoxyuridine (BzdU)

<400> SEQUENCE: 1
nnnccgcngn annnagcagn gagcgnnnan ncgccncaaa          40

<210> SEQ ID NO 2
<211> LENGTH: 39
<212> TYPE: DNA
<213> ORGANISM: Artificial Sequence
<220> FEATURE:
<223> OTHER INFORMATION: Synthetic (s003-H10022-T7_F09)
<220> FEATURE:
<221> NAME/KEY: misc_feature
<222> LOCATION: (2)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (5)..(6)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (10)..(11)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (13)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (19)..(20)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (24)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (29)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (31)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (37)
<223> OTHER INFORMATION: nucleotide base including that a benzyl group
      is introduced to 5-position of pyrimidine group of deoxyuridine
      (BzdU)

<400> SEQUENCE: 2
cncgnngacn nanccaccnn cagnagggnc ngagcgncg          39

<210> SEQ ID NO 3
<211> LENGTH: 40
<212> TYPE: DNA
<213> ORGANISM: Artificial Sequence
<220> FEATURE:
<223> OTHER INFORMATION: Synthetic (s003-H10011-T7_C08)
<220> FEATURE:
<221> NAME/KEY: misc_feature
<222> LOCATION: (1)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (3)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (6)..(8)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (15)..(16)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (21)..(22)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (32)..(35)

<400> SEQUENCE: 3
nangannngg cagannaaac nnccgcagca gnnnncccgg                40

<210> SEQ ID NO 4
<211> LENGTH: 40
<212> TYPE: DNA
<213> ORGANISM: Artificial Sequence
<220> FEATURE:
<223> OTHER INFORMATION: Synthetic (s003-H10012-T7_D08)
<220> FEATURE:
<221> NAME/KEY: misc_feature
<222> LOCATION: (6)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (10)..(11)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (15)..(16)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (18)..(20)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (27)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (29)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (32)..(33)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (35)..(36)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (40)
<223> OTHER INFORMATION: nucleotide base including that a benzyl group
      is introduced to 5-position of pyrimidine group of deoxyuridine
      (BzdU)

<400> SEQUENCE: 4
cgcagnccgn ngacnnannn gcaccgngng anngnncagn                    40

<210> SEQ ID NO 5
<211> LENGTH: 40
<212> TYPE: DNA
<213> ORGANISM: Artificial Sequence
<220> FEATURE:
<223> OTHER INFORMATION: Synthetic (s003-H10019-T7_C09)
<220> FEATURE:
<221> NAME/KEY: misc_feature
<222> LOCATION: (4)..(5)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (9)..(10)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (12)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (15)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (23)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (28)..(29)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (40)
<223> OTHER INFORMATION: nucleotide base including that a benzyl group
      is introduced to 5-position of pyrimidine group of deoxyuridine
      (BzdU)

<400> SEQUENCE: 5
gcgnngacnn ancanccccc agncggcnng caggccggcn            40

<210> SEQ ID NO 6
<211> LENGTH: 40
<212> TYPE: DNA
<213> ORGANISM: Artificial Sequence
<220> FEATURE:
<223> OTHER INFORMATION: Synthetic (s003-H10026-T7_B10)
<220> FEATURE:
<221> NAME/KEY: misc_feature
<222> LOCATION: (2)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (6)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (9)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (11)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (13)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (16)..(18)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (20)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (22)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (25)
<223> OTHER INFORMATION: vnucleotide base including that a benzyl group
      is introduced to 5-position of pyrimidine group of deoxyuridine
      (BzdU)
<220> FEATURE:
<221> NAME/KEY: misc_feature
<222> LOCATION: (29)..(31)
<223> OTHER INFORMATION: nucleotide base including that a benzyl group
      is introduced to 5-position of pyrimidine group of deoxyuridine
      (BzdU)

<400> SEQUENCE: 6
gnaaanagng ngngannngn gnaancagnn nacagacggg            40

<210> SEQ ID NO 7
<211> LENGTH: 41
<212> TYPE: DNA
<213> ORGANISM: Artificial Sequence
<220> FEATURE:
<223> OTHER INFORMATION: Synthetic (s003-H10001-T7_A07)
<220> FEATURE:
<221> NAME/KEY: misc_feature
<222> LOCATION: (2)..(3)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (7)..(8)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (11)..(13)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (19)..(20)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (22)..(23)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (27)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (37)..(38)
<223> OTHER INFORMATION: nucleotide base including that a benzyl group
      is introduced to 5-position of pyrimidine group of deoxyuridine
      (BzdU)

<400> SEQUENCE: 7
gnngacnnga nnnggggacnn gnncagnaac gcagccnnga c                41

<210> SEQ ID NO 8
<211> LENGTH: 40
<212> TYPE: DNA
<213> ORGANISM: Artificial Sequence
<220> FEATURE:
<223> OTHER INFORMATION: Synthetic (s003-H10004-T7_D07)
<220> FEATURE:
<221> NAME/KEY: misc_feature
<222> LOCATION: (1)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (6)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (9)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (11)
<223> OTHER INFORMATION: nucleotide base including that a benzyl group
      is introduced to 5-position of pyrimidine group of deoxyuridine

```
                (BzdU)
<220> FEATURE:
<221> NAME/KEY: misc_feature
<222> LOCATION: (15)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (17)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (19)..(20)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (22)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (28)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (30)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (34)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (36)
<223> OTHER INFORMATION: nucleotide base including that a benzyl group
      is introduced to 5-position of pyrimidine group of deoxyuridine
      (BzdU)

<400> SEQUENCE: 8
ncggcnggnc ngcgngngnn gncggcangn agancncgcg                              40

<210> SEQ ID NO 9
<211> LENGTH: 40
<212> TYPE: DNA
<213> ORGANISM: Artificial Sequence
<220> FEATURE:
<223> OTHER INFORMATION: Synthetic (s003-H10038-T7_D07)
<220> FEATURE:
<221> NAME/KEY: misc_feature
<222> LOCATION: (3)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (6)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (8)
<223> OTHER INFORMATION: nucleotide base including that a benzyl group
      is introduced to 5-position of pyrimidine group of deoxyuridine
      (BzdU)
```

<220> FEATURE:
<221> NAME/KEY: misc_feature
<222> LOCATION: (10)..(11)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (13)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (21)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (23)..(25)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (27)..(28)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (39)..(40)
<223> OTHER INFORMATION: nucleotide base including that a benzyl group
      is introduced to 5-position of pyrimidine group of deoxyuridine
      (BzdU)

<400> SEQUENCE: 9
agngcncnan nangccgggc nannnanncc cggggcggnn                           40

<210> SEQ ID NO 10
<211> LENGTH: 40
<212> TYPE: DNA
<213> ORGANISM: Artificial Sequence
<220> FEATURE:
<223> OTHER INFORMATION: Synthetic (s003-H10006-T7_D07)
<220> FEATURE:
<221> NAME/KEY: misc_feature
<222> LOCATION: (1)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (6)..(7)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (11)..(12)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (16)..(17)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (19)
<223> OTHER INFORMATION: nucleotide base including that a benzyl group
      is introduced to 5-position of pyrimidine group of deoxyuridine
      (BzdU)
<220> FEATURE:

```
<221> NAME/KEY: misc_feature
<222> LOCATION: (21)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (25)..(26)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (30)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (38)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (40)
<223> OTHER INFORMATION: nucleotide base including that a benzyl group
      is introduced to 5-position of pyrimidine group of deoxyuridine
      (BzdU)

<400> SEQUENCE: 10
ncagcnnccg nngacnnana ncccnncagn gaagcccncn                              40

<210> SEQ ID NO 11
<211> LENGTH: 40
<212> TYPE: DNA
<213> ORGANISM: Artificial Sequence
<220> FEATURE:
<223> OTHER INFORMATION: Synthetic (s003-H10002-T7_D07)
<220> FEATURE:
<221> NAME/KEY: misc_feature
<222> LOCATION: (7)..(8)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (15)..(16)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (20)..(21)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (23)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (25)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (29)..(30)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
```

<222> LOCATION: (34)
<223> OTHER INFORMATION: nucleotide base including that a benzyl group
      is introduced to 5-position of pyrimidine group of deoxyuridine
      (BzdU)

<400> SEQUENCE: 11
ggggagnnaa cgcgnngaan nangncccnn cagncggcac                              40

<210> SEQ ID NO 12
<211> LENGTH: 40
<212> TYPE: DNA
<213> ORGANISM: Artificial Sequence
<220> FEATURE:
<223> OTHER INFORMATION: Synthetic (s003-H10014-T7_D07)
<220> FEATURE:
<221> NAME/KEY: misc_feature
<222> LOCATION: (7)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (11)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (15)..(16)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (20)..(21)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (23)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (25)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (29)..(30)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (34)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (37)
<223> OTHER INFORMATION: nucleotide base including that a benzyl group
      is introduced to 5-position of pyrimidine group of deoxyuridine
      (BzdU)

<400> SEQUENCE: 12
gggaagngaa ngcgnngaan nangncccnn cagncancac                              40

<210> SEQ ID NO 13
<211> LENGTH: 40
<212> TYPE: DNA

```
<213> ORGANISM: Artificial Sequence
<220> FEATURE:
<223> OTHER INFORMATION: Synthetic (s003-H10033-T7_D07)
<220> FEATURE:
<221> NAME/KEY: misc_feature
<222> LOCATION: (3)..(4)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (6)..(7)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (11)..(12)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (16)..(18)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (23)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (25)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (29)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (32)
<223> OTHER INFORMATION: nucleotide base including that a benzyl group
      is introduced to 5-position of pyrimidine group of deoxyuridine
      (BzdU)

<400> SEQUENCE: 13
gcnncnncga nngaannnaa ganangcgnc cncagacaca                          40

<210> SEQ ID NO 14
<211> LENGTH: 42
<212> TYPE: DNA
<213> ORGANISM: Artificial Sequence
<220> FEATURE:
<223> OTHER INFORMATION: Synthetic (s003-H10020-T7_D07)
<220> FEATURE:
<221> NAME/KEY: misc_feature
<222> LOCATION: (1)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (3)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (5)..(8)
<223> OTHER INFORMATION: nucleotide base including that a benzyl group
``` is introduced to 5-position of pyrimidine group of deoxyuridine
        (BzdU)
<220> FEATURE:
<221> NAME/KEY: misc_feature
<222> LOCATION: (15)..(16)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (20)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (28)..(31)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (37)
<223> OTHER INFORMATION: nucleotide base including that a benzyl group
        is introduced to 5-position of pyrimidine group of deoxyuridine
        (BzdU)

<400> SEQUENCE: 14
nangnnnngg aggannaaan cccgcgannn ncagagngcc cc                           42

<210> SEQ ID NO 15
<211> LENGTH: 40
<212> TYPE: DNA
<213> ORGANISM: Artificial Sequence
<220> FEATURE:
<223> OTHER INFORMATION: Synthetic (S033-C1-01-M13-20R_A01)
<220> FEATURE:
<221> NAME/KEY: misc_feature
<222> LOCATION: (2)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (5)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (9)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (12)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (16)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (19)..(22)
<223> OTHER INFORMATION: nucleotide base including that a benzyl group
        is introduced to 5-position of pyrimidine group of deoxyuridine
        (BzdU)
<220> FEATURE:
<221> NAME/KEY: misc_feature
<222> LOCATION: (24)
<223> OTHER INFORMATION: nucleotide base including that a benzyl group
        is introduced to 5-position of pyrimidine group of deoxyuridine

```
         (BzdU)
<220> FEATURE:
<221> NAME/KEY: misc_feature
<222> LOCATION: (26)..(27)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (31)..(33)
<223> OTHER INFORMATION: nucleotide base including that a benzyl group
      is introduced to 5-position of pyrimidine group of deoxyuridine
      (BzdU)

<400> SEQUENCE: 15
gnaanaaana gngacngann nngngnnccg nnnacaccaa                           40

<210> SEQ ID NO 16
<211> LENGTH: 40
<212> TYPE: DNA
<213> ORGANISM: Artificial Sequence
<220> FEATURE:
<223> OTHER INFORMATION: Synthetic (S033-C1-10-M13-20R_B02)
<220> FEATURE:
<221> NAME/KEY: misc_feature
<222> LOCATION: (5)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (12)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (21)..(22)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (36)
<223> OTHER INFORMATION: nucleotide base including that a benzyl group
      is introduced to 5-position of pyrimidine group of deoxyuridine
      (BzdU)

<400> SEQUENCE: 16
accanagcac gnaacggagc nngcgcccaa ccgcanacac                           40

<210> SEQ ID NO 17
<211> LENGTH: 40
<212> TYPE: DNA
<213> ORGANISM: Artificial Sequence
<220> FEATURE:
<223> OTHER INFORMATION: Synthetic (S033-C1-11-M13-20R_C02)
<220> FEATURE:
<221> NAME/KEY: misc_feature
<222> LOCATION: (2)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (4)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (7)
<223> OTHER INFORMATION: nucleotide base including that a benzyl group
      is introduced to 5-position of pyrimidine group of deoxyuridine
      (BzdU)
```

<220> FEATURE:
<221> NAME/KEY: misc_feature
<222> LOCATION: (11)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (14)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (17)..(18)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (21)..(24)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (26)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (29)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (33)..(35)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (39)
<223> OTHER INFORMATION: nucleotide base including that a benzyl group
      is introduced to 5-position of pyrimidine group of deoxyuridine
      (BzdU)

<400> SEQUENCE: 17
angnganaaa nagnaannga nnnngnacnc agnnnacana                                40

<210> SEQ ID NO 18
<211> LENGTH: 40
<212> TYPE: DNA
<213> ORGANISM: Artificial Sequence
<220> FEATURE:
<223> OTHER INFORMATION: Synthetic (S033-C1-12-M13-20R_D02)
<220> FEATURE:
<221> NAME/KEY: misc_feature
<222> LOCATION: (3)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (6)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (10)
<223> OTHER INFORMATION: nucleotide base including that a benzyl group
      is introduced to 5-position of pyrimidine group of deoxyuridine
      (BzdU)
<220> FEATURE:

```
<221> NAME/KEY: misc_feature
<222> LOCATION: (13)..(15)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (17)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (20)..(23)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (25)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (28)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (32)..(34)
<223> OTHER INFORMATION: nucleotide base including that a benzyl group
      is introduced to 5-position of pyrimidine group of deoxyuridine
      (BzdU)

<400> SEQUENCE: 18 gancanaaaan agnnncngan nnngnagncc gnnnacgaga                          40

<210> SEQ ID NO 19
<211> LENGTH: 40
<212> TYPE: DNA
<213> ORGANISM: Artificial Sequence
<220> FEATURE:
<223> OTHER INFORMATION: Synthetic (S033-C1-17-M13-20R_A03)
<220> FEATURE:
<221> NAME/KEY: misc_feature
<222> LOCATION: (7)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (12)..(13)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (17)..(18)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (20)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (22)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
```

```
<222> LOCATION: (28)..(29)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (33)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (38)
<223> OTHER INFORMATION: nucleotide base including that a benzyl group
      is introduced to 5-position of pyrimidine group of deoxyuridine
      (BzdU)

<400> SEQUENCE: 19
ggcaccnccc cnngacnnan anccaccnnc agnggggngc                              40

<210> SEQ ID NO 20
<211> LENGTH: 40
<212> TYPE: DNA
<213> ORGANISM: Artificial Sequence
<220> FEATURE:
<223> OTHER INFORMATION: Synthetic (S033-C1-02-M13-20R_B01)
<220> FEATURE:
<221> NAME/KEY: misc_feature
<222> LOCATION: (4)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (7)..(12)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (15)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (17)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (24)..(27)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (29)
<223> OTHER INFORMATION: nucleotide base including that a benzyl group
      is introduced to 5-position of pyrimidine group of deoxyuridine
      (BzdU)

<400> SEQUENCE: 20
acgngcnnnn nnaangnacc gggnnnngnc cgggcagcga                              40

<210> SEQ ID NO 21
<211> LENGTH: 40
<212> TYPE: DNA
<213> ORGANISM: Artificial Sequence
<220> FEATURE:
<223> OTHER INFORMATION: Synthetic (S033-C1-25-M13-20R_A04)
<220> FEATURE:
<221> NAME/KEY: misc_feature
<222> LOCATION: (1)
```

<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (5)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (10)..(11)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (15)..(16)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (18)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (20)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (24)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (28)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (31)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (34)..(35)
<223> OTHER INFORMATION: nucleotide base including that a benzyl group
       is introduced to 5-position of pyrimidine group of deoxyuridine
       (BzdU)
<220> FEATURE:
<221> NAME/KEY: misc_feature
<222> LOCATION: (39)
<223> OTHER INFORMATION: nucleotide base including that a benzyl group
       is introduced to 5-position of pyrimidine group of deoxyuridine
       (BzdU)

<400> SEQUENCE: 21
nacgngccgn ngacnnanan cccncagngc nccnncccnc                             40

<210> SEQ ID NO 22
<211> LENGTH: 41
<212> TYPE: DNA
<213> ORGANISM: Artificial Sequence
<220> FEATURE:
<223> OTHER INFORMATION: Synthetic (S033-C1-37-M13-20R_E05)
<220> FEATURE:
<221> NAME/KEY: misc_feature
<222> LOCATION: (3)
<223> OTHER INFORMATION: nucleotide base including that a benzyl group is introduced to 5-position of pyrimidine group of deoxyuridine
(BzdU)
<220> FEATURE:
<221> NAME/KEY: misc_feature
<222> LOCATION: (10)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (13)..(14)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (19)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (26)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (28)..(30)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (33)
<223> OTHER INFORMATION: nucleotide base including that a benzyl group
is introduced to 5-position of pyrimidine group of deoxyuridine
(BzdU)

<400> SEQUENCE: 22
cgncagagcn ggnngcggng cccggnannn gcnccggcgc c                    41

<210> SEQ ID NO 23
<211> LENGTH: 40
<212> TYPE: DNA
<213> ORGANISM: Artificial Sequence
<220> FEATURE:
<223> OTHER INFORMATION: Synthetic (S033-C1-46-M13-20R_E05)
<220> FEATURE:
<221> NAME/KEY: misc_feature
<222> LOCATION: (1)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (5)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (8)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (10)
<223> OTHER INFORMATION: nucleotide base including that a benzyl group
is introduced to 5-position of pyrimidine group of deoxyuridine
(BzdU)
<220> FEATURE:
<221> NAME/KEY: misc_feature
<222> LOCATION: (12)
<223> OTHER INFORMATION: nucleotide base including that a benzyl group
is introduced to 5-position of pyrimidine group of deoxyuridine

```
(BzdU)
<220> FEATURE:
<221> NAME/KEY: misc_feature
<222> LOCATION: (15)..(18)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (20)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (22)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (25)..(27)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (29)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (33)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (40)
<223> OTHER INFORMATION: nucleotide base including that a benzyl group
      is introduced to 5-position of pyrimidine group of deoxyuridine
      (BzdU)

<400> SEQUENCE: 23
naaanagngn cnaannnngn ancgnnnanc gcnagaagcn                           40

<210> SEQ ID NO 24
<211> LENGTH: 40
<212> TYPE: DNA
<213> ORGANISM: Artificial Sequence
<220> FEATURE:
<223> OTHER INFORMATION: Synthetic (S033-C1-16-M13-20R_E05)
<220> FEATURE:
<221> NAME/KEY: misc_feature
<222> LOCATION: (8)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (10)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (12)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (15)..(17)
<223> OTHER INFORMATION: nucleotide base including that a benzyl group
      is introduced to 5-position of pyrimidine group of deoxyuridine
      (BzdU)
```

<220> FEATURE:
<221> NAME/KEY: misc_feature
<222> LOCATION: (25)..(28)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (30)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (33)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (36)
<223> OTHER INFORMATION: nucleotide base including that a benzyl group
      is introduced to 5-position of pyrimidine group of deoxyuridine
      (BzdU)

<400> SEQUENCE: 24
acgaaaancn anacnnncaa ggggnnnngn acnaancccg                              40

<210> SEQ ID NO 25
<211> LENGTH: 39
<212> TYPE: DNA
<213> ORGANISM: Artificial Sequence
<220> FEATURE:
<223> OTHER INFORMATION: Synthetic (S033-C1-30-M13-20R_E05)
<220> FEATURE:
<221> NAME/KEY: misc_feature
<222> LOCATION: (2)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (5)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (9)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (13)..(14)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (20)..(21)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (25)..(26)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (28)
<223> OTHER INFORMATION: nucleotide base including that a benzyl group
      is introduced to 5-position of pyrimidine group of deoxyuridine
      (BzdU)
<220> FEATURE:

```
<221> NAME/KEY: misc_feature
<222> LOCATION: (30)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (34)
<223> OTHER INFORMATION: nucleotide base including that a benzyl group
      is introduced to 5-position of pyrimidine group of deoxyuridine
      (BzdU)
<220> FEATURE:
<221> NAME/KEY: misc_feature
<222> LOCATION: (38)
<223> OTHER INFORMATION: nucleotide base including that a benzyl group
      is introduced to 5-position of pyrimidine group of deoxyuridine
      (BzdU)

<400> SEQUENCE: 25
anggnggcna acnnggccgn ngacnnanan cccncagng                              39

<210> SEQ ID NO 26
<211> LENGTH: 40
<212> TYPE: DNA
<213> ORGANISM: Artificial Sequence
<220> FEATURE:
<223> OTHER INFORMATION: Synthetic (S033-D1-01-M13-20R_A07)
<220> FEATURE:
<221> NAME/KEY: misc_feature
<222> LOCATION: (8)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (11)..(13)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (18)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (21)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (25)..(26)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (33)..(34)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (36)..(37)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (39)
<223> OTHER INFORMATION: a nucleotide including a naphthyl group
      introduced to 5-position of pyrimidine group of deoxyuridine
      (NapdU)

<400> SEQUENCE: 26
```
caacggcnag nnncacgnga naaanncaca gcnngnnanc 40

<210> SEQ ID NO 27
<211> LENGTH: 40
<212> TYPE: DNA
<213> ORGANISM: Artificial Sequence
<220> FEATURE:
<223> OTHER INFORMATION: Synthetic (S033-D1-10-M13-20R_B08)
<220> FEATURE:
<221> NAME/KEY: misc_feature
<222> LOCATION: (1)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (8)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (10)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (14)..(16)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (18)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (24)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (28)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (33)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (36)
<223> OTHER INFORMATION: a nucleotide including a naphthyl group
introduced to 5-position of pyrimidine group of deoxyuridine
(NapdU)

<400> SEQUENCE: 27
nacaagangn gaannnancc ccgngagngg cancgngacc 40

<210> SEQ ID NO 28
<211> LENGTH: 40
<212> TYPE: DNA
<213> ORGANISM: Artificial Sequence
<220> FEATURE:
<223> OTHER INFORMATION: Synthetic (S033-D1-12-M13-20R_D08)
<220> FEATURE:
<221> NAME/KEY: misc_feature
<222> LOCATION: (4)

```
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (6)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (12)..(13)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (18)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (24)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (26)..(28)
<223> OTHER INFORMATION: a nucleotide including a naphthyl group
      introduced to 5-position of pyrimidine group of deoxyuridine
      (NapdU)

<400> SEQUENCE: 28
gcanangagg gnnaggcnag ccancnnngg ggcagcagga                    40

<210> SEQ ID NO 29
<211> LENGTH: 40
<212> TYPE: DNA
<213> ORGANISM: Artificial Sequence
<220> FEATURE:
<223> OTHER INFORMATION: Synthetic (S033-D1-19-M13-20R_C09)
<220> FEATURE:
<221> NAME/KEY: misc_feature
<222> LOCATION: (1)..(3)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (8)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (11)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (21)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (25)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (31)
<223> OTHER INFORMATION: a nucleotide including a naphthyl group
``` introduced to 5-position of pyrimidine group of deoxyuridine
(NapdU)
<220> FEATURE:
<221> NAME/KEY: misc_feature
<222> LOCATION: (33)
<223> OTHER INFORMATION: a nucleotide including a naphthyl group
introduced to 5-position of pyrimidine group of deoxyuridine
(NapdU)

<400> SEQUENCE: 29 nnngggngg naggacacgg ngaanaaaga ncnggcccgc                                40

<210> SEQ ID NO 30
<211> LENGTH: 40
<212> TYPE: DNA
<213> ORGANISM: Artificial Sequence
<220> FEATURE:
<223> OTHER INFORMATION: Synthetic (S033-D1-32-M13-20R_H10)
<220> FEATURE:
<221> NAME/KEY: misc_feature
<222> LOCATION: (4)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (6)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (10)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (14)..(15)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (19)..(23)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (33)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (38)
<223> OTHER INFORMATION: a nucleotide including a naphthyl group
introduced to 5-position of pyrimidine group of deoxyuridine
(NapdU)

<400> SEQUENCE: 30
caangnaagn gcannaaann nnngccaagg ccncagcngc                                40

<210> SEQ ID NO 31
<211> LENGTH: 40
<212> TYPE: DNA
<213> ORGANISM: Artificial Sequence
<220> FEATURE:
<223> OTHER INFORMATION: Synthetic (S033-D1-07-M13-20R_G07)
<220> FEATURE:
<221> NAME/KEY: misc_feature
<222> LOCATION: (1)
<223> OTHER INFORMATION: a nucleotide including a naphthyl group
introduced to 5-position of pyrimidine group of deoxyuridine (NapdU)
<220> FEATURE:
<221> NAME/KEY: misc_feature
<222> LOCATION: (7)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (9)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (13)..(15)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (17)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (23)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (37)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (39)
<223> OTHER INFORMATION: a nucleotide including a naphthyl group
      introduced to 5-position of pyrimidine group of deoxyuridine
      (NapdU)

<400> SEQUENCE: 31
ncaagangng aannnancac cgnggggcga aggaccngng                                40

<210> SEQ ID NO 32
<211> LENGTH: 40
<212> TYPE: DNA
<213> ORGANISM: Artificial Sequence
<220> FEATURE:
<223> OTHER INFORMATION: Synthetic (S033-D1-02-M13-20R_G07)
<220> FEATURE:
<221> NAME/KEY: misc_feature
<222> LOCATION: (14)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (18)..(19)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (24)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (26)..(27)
<223> OTHER INFORMATION: a nucleotide including a naphthyl group
      introduced to 5-position of pyrimidine group of deoxyuridine
      (NapdU)

<220> FEATURE:
<221> NAME/KEY: misc_feature
<222> LOCATION: (33)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (36)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (38)..(40)
<223> OTHER INFORMATION: a nucleotide including a naphthyl group
introduced to 5-position of pyrimidine group of deoxyuridine
(NapdU)

<400> SEQUENCE: 32
ggacacacgg gganaaannc acancnngac canccngnnn                          40

<210> SEQ ID NO 33
<211> LENGTH: 40
<212> TYPE: DNA
<213> ORGANISM: Artificial Sequence
<220> FEATURE:
<223> OTHER INFORMATION: Synthetic (S033-D1-28-M13-20R_G07)
<220> FEATURE:
<221> NAME/KEY: misc_feature
<222> LOCATION: (9)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (15)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (22)..(23)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (25)..(26)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (34)
<223> OTHER INFORMATION: a nucleotide including a naphthyl group
introduced to 5-position of pyrimidine group of deoxyuridine
(NapdU)
<220> FEATURE:
<221> NAME/KEY: misc_feature
<222> LOCATION: (36)
<223> OTHER INFORMATION: a nucleotide including a naphthyl group
introduced to 5-position of pyrimidine group of deoxyuridine
(NapdU)

<400> SEQUENCE: 33
gcacagganc ggganaagcg cnncnncaac aaangnacgg                          40

<210> SEQ ID NO 34
<211> LENGTH: 40
<212> TYPE: DNA
<213> ORGANISM: Artificial Sequence
<220> FEATURE:
<223> OTHER INFORMATION: Synthetic (S033-D1-44-M13-20R_G07)
<220> FEATURE:

```
<221> NAME/KEY: misc_feature
<222> LOCATION: (1)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (11)..(12)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (15)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (21)..(22)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (26)..(27)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (31)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (37)..(38)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (40)
<223> OTHER INFORMATION: a nucleotide including a naphthyl group
      introduced to 5-position of pyrimidine group of deoxyuridine
      (NapdU)

<400> SEQUENCE: 34
ncggcaaaaa nnaangcgac nnacanngcc nccaacnncn                    40

<210> SEQ ID NO 35
<211> LENGTH: 39
<212> TYPE: DNA
<213> ORGANISM: Artificial Sequence
<220> FEATURE:
<223> OTHER INFORMATION: Synthetic (S033-D1-46-M13-20R_G07)
<220> FEATURE:
<221> NAME/KEY: misc_feature
<222> LOCATION: (8)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (10)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (14)..(15)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
```

<222> LOCATION: (18)..(19)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (22)..(26)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (30)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (34)
<223> OTHER INFORMATION: a nucleotide including a naphthyl group
      introduced to 5-position of pyrimidine group of deoxyuridine
      (NapdU)

<400> SEQUENCE: 35
aacgcaangn aagnnggnna annnnngcgn gagncccgg                        39

<210> SEQ ID NO 36
<211> LENGTH: 40
<212> TYPE: DNA
<213> ORGANISM: Artificial Sequence
<220> FEATURE:
<223> OTHER INFORMATION: Synthetic (S033-D1-27-M13-20R_G07)
<220> FEATURE:
<221> NAME/KEY: misc_feature
<222> LOCATION: (3)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (5)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (9)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (13)..(14)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (17)..(21)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (32)
<223> OTHER INFORMATION: a nucleotide including a naphthyl group
      introduced to 5-position of pyrimidine group of deoxyuridine
      (NapdU)

<400> SEQUENCE: 36
cangnaagng aannaannnn ngcgaagggc anggaaaggc                       40

<210> SEQ ID NO 37
<211> LENGTH: 40
<212> TYPE: DNA

```
<213> ORGANISM: Artificial Sequence
<220> FEATURE:
<223> OTHER INFORMATION: Synthetic (S033-D1-37-M13-20R_G07)
<220> FEATURE:
<221> NAME/KEY: misc_feature
<222> LOCATION: (2)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (4)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (7)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (10)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (12)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (15)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (17)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (22)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (27)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (31)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (38)..(40)
<223> OTHER INFORMATION: a nucleotide including a naphthyl group
      introduced to 5-position of pyrimidine group of deoxyuridine
      (NapdU)

<400> SEQUENCE: 37
gncnggnccn ancgngngcg gngccgngac nacagaannn                            40

<210> SEQ ID NO 38
<211> LENGTH: 40
<212> TYPE: DNA
<213> ORGANISM: Artificial Sequence
```

```
<220> FEATURE:
<223> OTHER INFORMATION: Synthetic (S033-D1-22-M13-20R_G07)
<220> FEATURE:
<221> NAME/KEY: misc_feature
<222> LOCATION: (2)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (7)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (9)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (12)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (22)..(23)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (25)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (37)
<223> OTHER INFORMATION: a nucleotide including a naphthyl group
      introduced to 5-position of pyrimidine group of deoxyuridine
      (NapdU)

<400> SEQUENCE: 38
anagggngng ancgcagagg gnnancaaag aggacangga                            40

<210> SEQ ID NO 39
<211> LENGTH: 40
<212> TYPE: DNA
<213> ORGANISM: Artificial Sequence
<220> FEATURE:
<223> OTHER INFORMATION: Synthetic (S033-D1-31-M13-20R_G07)
<220> FEATURE:
<221> NAME/KEY: misc_feature
<222> LOCATION: (1)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (4)..(5)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (8)..(11)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (13)
<223> OTHER INFORMATION: a nucleotide including a naphthyl group
      introduced to 5-position of pyrimidine group of deoxyuridine
```

```
          (NapdU)
<220> FEATURE:
<221> NAME/KEY: misc_feature
<222> LOCATION: (20)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (36)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (39)
<223> OTHER INFORMATION: a nucleotide including a naphthyl group
      introduced to 5-position of pyrimidine group of deoxyuridine
      (NapdU)

<400> SEQUENCE: 39
ngcnnacnnn nangacacgn cccgcacaaa aggccnagng                           40

<210> SEQ ID NO 40
<211> LENGTH: 40
<212> TYPE: DNA
<213> ORGANISM: Artificial Sequence
<220> FEATURE:
<223> OTHER INFORMATION: Synthetic (S033-D1-18-M13-20R_G07)
<220> FEATURE:
<221> NAME/KEY: misc_feature
<222> LOCATION: (1)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (3)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (7)..(10)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (14)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (21)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (24)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (27)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (38)
<223> OTHER INFORMATION: a nucleotide including a naphthyl group
      introduced to 5-position of pyrimidine group of deoxyuridine
      (NapdU)
```

<400> SEQUENCE: 40
nangccnnnn gacnacaccc nganccnacc caccaccnca                                40

<210> SEQ ID NO 41
<211> LENGTH: 40
<212> TYPE: DNA
<213> ORGANISM: Artificial Sequence
<220> FEATURE:
<223> OTHER INFORMATION: Synthetic (S033-D1-42-M13-20R_G07)
<220> FEATURE:
<221> NAME/KEY: misc_feature
<222> LOCATION: (2)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (8)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (10)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (14)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (19)..(20)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (23)..(27)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (38)
<223> OTHER INFORMATION: a nucleotide including a naphthyl group
      introduced to 5-position of pyrimidine group of deoxyuridine
      (NapdU)

<400> SEQUENCE: 41
gngggcangn aagnaggann aannnnngaa ccaccagnag                                40

<210> SEQ ID NO 42
<211> LENGTH: 42
<212> TYPE: DNA
<213> ORGANISM: Artificial Sequence
<220> FEATURE:
<223> OTHER INFORMATION: Synthetic (S033-D1-45-M13-20R_G07)
<220> FEATURE:
<221> NAME/KEY: misc_feature
<222> LOCATION: (2)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (6)..(7)
<223> OTHER INFORMATION: a nucleotide including a naphthyl group
      introduced to 5-position of pyrimidine group of deoxyuridine
      (NapdU)
<220> FEATURE:

```
<221> NAME/KEY: misc_feature
<222> LOCATION: (9)..(11)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (13)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (15)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (18)
<223> OTHER INFORMATION: a nucleotide including a naphthyl group
      introduced to 5-position of pyrimidine group of deoxyuridine
      (NapdU)

<400> SEQUENCE: 42
cnccanngnn nananganaa ggcaggcaag gggcccaccg ga                    42

<210> SEQ ID NO 43
<211> LENGTH: 40
<212> TYPE: DNA
<213> ORGANISM: Artificial Sequence
<220> FEATURE:
<223> OTHER INFORMATION: Synthetic (S033-D1-08-M13-20R_H07)
<220> FEATURE:
<221> NAME/KEY: misc_feature
<222> LOCATION: (6)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (8)..(9)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (13)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (15)..(16)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (21)..(22)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (24)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (30)..(32)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
```

```
<222> LOCATION: (39)
<223> OTHER INFORMATION: a nucleotide including a naphthyl group
      introduced to 5-position of pyrimidine group of deoxyuridine
      (NapdU)

<400> SEQUENCE: 43
ccccangnna aangnnggcg nncngcggan nncggcgana                              40

<210> SEQ ID NO 44
<211> LENGTH: 40
<212> TYPE: DNA
<213> ORGANISM: Artificial Sequence
<220> FEATURE:
<223> OTHER INFORMATION: Synthetic (S033-D1-16-M13-20R_H08)
<220> FEATURE:
<221> NAME/KEY: misc_feature
<222> LOCATION: (1)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (3)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (10)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (15)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (19)..(20)
<223> OTHER INFORMATION: a nucleotide including a naphthyl group
      introduced to 5-position of pyrimidine group of deoxyuridine
      (NapdU)
<220> FEATURE:
<221> NAME/KEY: misc_feature
<222> LOCATION: (32)
<223> OTHER INFORMATION: a nucleotide including a naphthyl group
      introduced to 5-position of pyrimidine group of deoxyuridine
      (NapdU)

<400> SEQUENCE: 44
ngnggcaacn aggcnggcnn acgaaagcag gnagccgagg                              40

<210> SEQ ID NO 45
<211> LENGTH: 18
<212> TYPE: DNA
<213> ORGANISM: Artificial Sequence
<220> FEATURE:
<223> OTHER INFORMATION: Synthetic (primer)

<400> SEQUENCE: 45
tcagccgcca gccagttc                                                     18

<210> SEQ ID NO 46
<211> LENGTH: 18
<212> TYPE: DNA
<213> ORGANISM: Artificial Sequence
<220> FEATURE:
<223> OTHER INFORMATION: Synthetic (primer)

<400> SEQUENCE: 46
```
gaccagagca ccacagag                                                    18

<210> SEQ ID NO 47
<211> LENGTH: 17
<212> TYPE: DNA
<213> ORGANISM: Artificial Sequence
<220> FEATURE:
<223> OTHER INFORMATION: Synthetic (primer)

<400> SEQUENCE: 47
cgagcgtcct gcctttg                                                     17

<210> SEQ ID NO 48
<211> LENGTH: 17
<212> TYPE: DNA
<213> ORGANISM: Artificial Sequence
<220> FEATURE:
<223> OTHER INFORMATION: Synthetic (primer)

<400> SEQUENCE: 48
caccgacagc cacccag                                                     17

<210> SEQ ID NO 49
<211> LENGTH: 41
<212> TYPE: DNA
<213> ORGANISM: Artificial Sequence
<220> FEATURE:
<223> OTHER INFORMATION: Synthetic (aptamer sequence)

<400> SEQUENCE: 49
gttgacttga tttgggactt gttcagtaac gcagccttga c                          41

<210> SEQ ID NO 50
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 50
tttccgctgt atttagcagt gagcgtttat tcgcctcaaa                            40

<210> SEQ ID NO 51
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 51
tatgatttgg cagattaaac ttccgcagca gttttcccgg                            40

<210> SEQ ID NO 52
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 52
cgcagtccgt tgacttattt gcaccgtgtg attgttcagt                            40

<210> SEQ ID NO 53
<211> LENGTH: 40
<212> TYPE: DNA
<213> ORGANISM: Artificial Sequence

```
<220> FEATURE:
<223> OTHER INFORMATION: Synthetic (aptamer sequence)

<400> SEQUENCE: 53
gcgttgactt atcatccccc agtcggcttg caggccggct                              40

<210> SEQ ID NO 54
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 54
ctcgttgact tatctcacct tcagtagggt ctgagcgtcg                              40

<210> SEQ ID NO 55
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 55
gtaaatagtg tgtgatttgt gtaatcagtt tacagacggg                              40

<210> SEQ ID NO 56
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 56
tcggctggtc tgcgtgtgtt gtcggcatgt agatctcgcg                              40

<210> SEQ ID NO 57
<211> LENGTH: 7
<212> TYPE: DNA
<213> ORGANISM: Artificial Sequence
<220> FEATURE:
<223> OTHER INFORMATION: Synthetic (aptamer sequence)

<400> SEQUENCE: 57 tttattc                                                                   7

<210> SEQ ID NO 58
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 58
agtgctctat tatgccgggc tatttattcc cggggcggtt                              40

<210> SEQ ID NO 59
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 59
tttccgctgt atttagcagt gagcgtttat tcgcctcaaa                              40
```

<210> SEQ ID NO 60
<211> LENGTH: 11
<212> TYPE: DNA
<213> ORGANISM: Artificial Sequence
<220> FEATURE:
<223> OTHER INFORMATION: Synthetic (aptamer sequence)

<400> SEQUENCE: 60
cgttgactta t                                                           11

<210> SEQ ID NO 61
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 61
ctcgttgact tatctcacct tcagtagggt ctgagcgtcg                            40

<210> SEQ ID NO 62
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 62
gcgttgactt atcatccccc agtcggcttg caggccggct                            40

<210> SEQ ID NO 63
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 63
tcagcttccg ttgacttata tcccttcagt gaagccctct                            40

<210> SEQ ID NO 64
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 64
cgcagtccgt tgacttattt gcaccgtgtg attgttcagt                            40

<210> SEQ ID NO 65
<211> LENGTH: 7
<212> TYPE: DNA
<213> ORGANISM: Artificial Sequence
<220> FEATURE:
<223> OTHER INFORMATION: Synthetic (aptamer sequence)

<400> SEQUENCE: 65 ttcagta                                                                7

<210> SEQ ID NO 66
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 66
ggggagttaa cgcgttgaat tatgtccctt cagtcggcac                40

<210> SEQ ID NO 67
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 67
gggaagtgaa tgcgttgaat tatgtccctt cagtcatcac                40

<210> SEQ ID NO 68
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 68
ctcgttgact tatctcacct tcagtagggt ctgagcgtcg                40

<210> SEQ ID NO 69
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 69
tcagcttccg ttgacttata tcccttcagt gaagccctct                40

<210> SEQ ID NO 70
<211> LENGTH: 41
<212> TYPE: DNA
<213> ORGANISM: Artificial Sequence
<220> FEATURE:
<223> OTHER INFORMATION: Synthetic (aptamer sequence)

<400> SEQUENCE: 70
gttgacttga tttgggactt gttcagtaac gcagccttga c              41

<210> SEQ ID NO 71
<211> LENGTH: 8
<212> TYPE: DNA
<213> ORGANISM: Artificial Sequence
<220> FEATURE:
<223> OTHER INFORMATION: Synthetic (aptamer sequence)

<400> SEQUENCE: 71 ccttcagt                                                    8

<210> SEQ ID NO 72
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 72
ggggagttaa cgcgttgaat tatgtccctt cagtcggcac                40

<210> SEQ ID NO 73

```
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 73
gggaagtgaa tgcgttgaat tatgtccctt cagtcatcac                           40

<210> SEQ ID NO 74
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 74
ctcgttgact tatctcacct tcagtagggt ctgagcgtcg                           40

<210> SEQ ID NO 75
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 75
tcagcttccg ttgacttata tcccttcagt gaagccctct                           40

<210> SEQ ID NO 76
<211> LENGTH: 12
<212> TYPE: DNA
<213> ORGANISM: Artificial Sequence
<220> FEATURE:
<223> OTHER INFORMATION: Synthetic (aptamer sequence)

<400> SEQUENCE: 76
cgttgactta tc                                                         12

<210> SEQ ID NO 77
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 77
ctcgttgact tatctcacct tcagtagggt ctgagcgtcg                           40

<210> SEQ ID NO 78
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 78
gcgttgactt atcatccccc agtcggcttg caggccggct                           40

<210> SEQ ID NO 79
<211> LENGTH: 8
<212> TYPE: DNA
<213> ORGANISM: Artificial Sequence
<220> FEATURE:
<223> OTHER INFORMATION: Synthetic (aptamer sequence)

<400> SEQUENCE: 79
```

```
tgatttgg                                                           8

<210> SEQ ID NO 80
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 80
tatgatttgg cagattaaac ttccgcagca gttttcccgg                        40

<210> SEQ ID NO 81
<211> LENGTH: 41
<212> TYPE: DNA
<213> ORGANISM: Artificial Sequence
<220> FEATURE:
<223> OTHER INFORMATION: Synthetic (aptamer sequence)

<400> SEQUENCE: 81
gttgacttga tttgggactt gttcagtaac gcagccttga c                      41

<210> SEQ ID NO 82
<211> LENGTH: 9
<212> TYPE: DNA
<213> ORGANISM: Artificial Sequence
<220> FEATURE:
<223> OTHER INFORMATION: Synthetic (aptamer sequence)

<400> SEQUENCE: 82 tatgatttg                                                          9

<210> SEQ ID NO 83
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 83
tatgatttgg cagattaaac ttccgcagca gttttcccgg                        40

<210> SEQ ID NO 84
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 84
gtaaatagtg tgtgatttgt gtaatcagtt tacagacggg                        40

<210> SEQ ID NO 85
<211> LENGTH: 7
<212> TYPE: DNA
<213> ORGANISM: Artificial Sequence
<220> FEATURE:
<223> OTHER INFORMATION: Synthetic (aptamer sequence)

<400> SEQUENCE: 85 gattaaa                                                            7

<210> SEQ ID NO 86
<211> LENGTH: 40
<212> TYPE: DNA
```

```
<213> ORGANISM: Artificial Sequence
<220> FEATURE:
<223> OTHER INFORMATION: Synthetic (aptamer sequence)

<400> SEQUENCE: 86
tatgatttgg cagattaaac ttccgcagca gttttcccgg                              40

<210> SEQ ID NO 87
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 87
gcttcttcga ttgaatttaa gatatgcgtc ctcagacaca                              40

<210> SEQ ID NO 88
<211> LENGTH: 42
<212> TYPE: DNA
<213> ORGANISM: Artificial Sequence
<220> FEATURE:
<223> OTHER INFORMATION: Synthetic (aptamer sequence)

<400> SEQUENCE: 88
tatgttttgg aggattaaat cccgcgattt tcagagtgcc cc                           42

<210> SEQ ID NO 89
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 89
gtaataaata gtgactgatt ttgtgttccg tttacaccaa                              40

<210> SEQ ID NO 90
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 90
gtgtatgcgg ttgggcgcaa gctccgttac gtgctatggt                              40

<210> SEQ ID NO 91
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 91
atgtgataaa tagtaattga ttttgtactc agtttacata                              40

<210> SEQ ID NO 92
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 92
gatcataaat agtttctgat tttgtagtcc gtttacgaga                              40
```

<210> SEQ ID NO 93
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 93
ggcacctccc cttgacttat atccaccttc agtggggtgc                                40

<210> SEQ ID NO 94
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 94
acgtgctttt ttaatgtacc gggttttgtc cgggcagcga                                40

<210> SEQ ID NO 95
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 95
tacgtgccgt tgacttatat ccctcagtgc tccttccctc                                40

<210> SEQ ID NO 96
<211> LENGTH: 41
<212> TYPE: DNA
<213> ORGANISM: Artificial Sequence
<220> FEATURE:
<223> OTHER INFORMATION: Synthetic (aptamer sequence)

<400> SEQUENCE: 96
cgtcagagct ggttgcggtg cccggtattt gctccggcgc c                              41

<210> SEQ ID NO 97
<211> LENGTH: 9
<212> TYPE: DNA
<213> ORGANISM: Artificial Sequence
<220> FEATURE:
<223> OTHER INFORMATION: Synthetic (aptamer sequence)

<400> SEQUENCE: 97 ataaatagt                                                                   9

<210> SEQ ID NO 98
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 98
gatcataaat agtttctgat tttgtagtcc gtttacgaga                                40

<210> SEQ ID NO 99
<211> LENGTH: 40
<212> TYPE: DNA
<213> ORGANISM: Artificial Sequence
<220> FEATURE:

<223> OTHER INFORMATION: Synthetic (aptamer sequence)

<400> SEQUENCE: 99
gtaataaata gtgactgatt ttgtgttccg tttacaccaa           40

<210> SEQ ID NO 100
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 100
atgtgataaa tagtaattga ttttgtactc agtttacata           40

<210> SEQ ID NO 101
<211> LENGTH: 10
<212> TYPE: DNA
<213> ORGANISM: Artificial Sequence
<220> FEATURE:
<223> OTHER INFORMATION: Synthetic (aptamer sequence)

<400> SEQUENCE: 101
tgattttgta           10

<210> SEQ ID NO 102
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 102
gatcataaat agtttctgat tttgtagtcc gtttacgaga           40

<210> SEQ ID NO 103
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 103
taaatagtgt ctaattttgt atcgtttatc gctagaagct           40

<210> SEQ ID NO 104
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 104
gtaataaata gtgactgatt ttgtgttccg tttacaccaa           40

<210> SEQ ID NO 105
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 105
atgtgataaa tagtaattga ttttgtactc agtttacata           40

```
<210> SEQ ID NO 106
<211> LENGTH: 10
<212> TYPE: DNA
<213> ORGANISM: Artificial Sequence
<220> FEATURE:
<223> OTHER INFORMATION: Synthetic (aptamer sequence)

<400> SEQUENCE: 106
ctgattttgt                                                              10

<210> SEQ ID NO 107
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 107
gatcataaat agtttctgat tttgtagtcc gtttacgaga                             40

<210> SEQ ID NO 108
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 108
gtaataaata gtgactgatt ttgtgttccg tttacaccaa                             40

<210> SEQ ID NO 109
<211> LENGTH: 9
<212> TYPE: DNA
<213> ORGANISM: Artificial Sequence
<220> FEATURE:
<223> OTHER INFORMATION: Synthetic (aptamer sequence)

<400> SEQUENCE: 109 taaatagtg                                                                9

<210> SEQ ID NO 110
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 110
taaatagtgt ctaattttgt atcgtttatc gctagaagct                             40

<210> SEQ ID NO 111
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 111
gtaataaata gtgactgatt ttgtgttccg tttacaccaa                             40

<210> SEQ ID NO 112
<211> LENGTH: 9
<212> TYPE: DNA
<213> ORGANISM: Artificial Sequence
<220> FEATURE:
<223> OTHER INFORMATION: Synthetic (aptamer sequence)
```

```
<400> SEQUENCE: 112 ttttgtact                                                             9

<210> SEQ ID NO 113
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 113
gatcataaat agtttctgat tttgtagtcc gtttacgaga                          40

<210> SEQ ID NO 114
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 114
atgtgataaa tagtaattga ttttgtactc agtttacata                          40

<210> SEQ ID NO 115
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 115
acgaaaatct atactttcaa ggggttttgt actaatcccg                          40

<210> SEQ ID NO 116
<211> LENGTH: 11
<212> TYPE: DNA
<213> ORGANISM: Artificial Sequence
<220> FEATURE:
<223> OTHER INFORMATION: Synthetic (aptamer sequence)

<400> SEQUENCE: 116
tctgattttg t                                                         11

<210> SEQ ID NO 117
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 117
gatcataaat agtttctgat tttgtagtcc gtttacgaga                          40

<210> SEQ ID NO 118
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 118
taaatagtgt ctaattttgt atcgtttatc gctagaagct                          40

<210> SEQ ID NO 119
<211> LENGTH: 13
```

```
<212> TYPE: DNA
<213> ORGANISM: Artificial Sequence
<220> FEATURE:
<223> OTHER INFORMATION: Synthetic (aptamer sequence)

<400> SEQUENCE: 119
ttgacttata tcc                                                          13

<210> SEQ ID NO 120
<211> LENGTH: 39
<212> TYPE: DNA
<213> ORGANISM: Artificial Sequence
<220> FEATURE:
<223> OTHER INFORMATION: Synthetic (aptamer sequence)

<400> SEQUENCE: 120
atggtggcta acttggccgt tgacttatat ccctcagtg                              39

<210> SEQ ID NO 121
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 121
tacgtgccgt tgacttatat ccctcagtgc tccttccctc                             40

<210> SEQ ID NO 122
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 122
ggcacctccc cttgacttat atccaccttc agtggggtgc                             40

<210> SEQ ID NO 123
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 123
gataacaagc tgtgaattta tcacgtgaaa ctagccgttg                             40

<210> SEQ ID NO 124
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 124
tacaagatgt gaatttatcc ccgtgagtgg catcgtgacc                             40

<210> SEQ ID NO 125
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 125
```
gcatatgagg gttaggctag ccatctttgg ggcagcagga            40

<210> SEQ ID NO 126
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 126
tttggggtgg taggacacgg tgaataaaga tctggcccgc            40

<210> SEQ ID NO 127
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 127
caatgtaagt gcattaaatt tttgccaagg cctcagctgc            40

<210> SEQ ID NO 128
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 128
tcaagatgtg aatttatcac cgtggggcga aggacctgtg            40

<210> SEQ ID NO 129
<211> LENGTH: 12
<212> TYPE: DNA
<213> ORGANISM: Artificial Sequence
<220> FEATURE:
<223> OTHER INFORMATION: Synthetic (aptamer sequence)

<400> SEQUENCE: 129
tgtgaattta tc            12

<210> SEQ ID NO 130
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 130
aaacaggatg gtcaagatgt gaatttatcc ccgtgtgtcc            40

<210> SEQ ID NO 131
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 131
tacaagatgt gaatttatcc ccgtgagtgg catcgtgacc            40

<210> SEQ ID NO 132
<211> LENGTH: 40
<212> TYPE: DNA
<213> ORGANISM: Artificial Sequence

```
<220> FEATURE:
<223> OTHER INFORMATION: Synthetic (aptamer sequence)

<400> SEQUENCE: 132 tagggggcgct gtcaagatgt gaatttatcc cgtgatatcg                              40

<210> SEQ ID NO 133
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 133
aacgtcaagc tgtgaattta tcaccgtgta cgaaccacgg                              40

<210> SEQ ID NO 134
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 134
tcaagatgtg aatttatcac cgtggggcga aggacctgtg                              40

<210> SEQ ID NO 135
<211> LENGTH: 41
<212> TYPE: DNA
<213> ORGANISM: Artificial Sequence
<220> FEATURE:
<223> OTHER INFORMATION: Synthetic (aptamer sequence)

<400> SEQUENCE: 135
tccaagctgt gaatttatca ccgtgaaggc tgcagcccct a                            41

<210> SEQ ID NO 136
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 136
gataacaagc tgtgaattta tcacgtgaaa ctagccgttg                              40

<210> SEQ ID NO 137
<211> LENGTH: 8
<212> TYPE: DNA
<213> ORGANISM: Artificial Sequence
<220> FEATURE:
<223> OTHER INFORMATION: Synthetic (aptamer sequence)

<400> SEQUENCE: 137 ttatcccg                                                                  8

<210> SEQ ID NO 138
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 138
aaacaggatg gtcaagatgt gaatttatcc ccgtgtgtcc                              40
```

<210> SEQ ID NO 139
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 139
tacaagatgt gaatttatcc ccgtgagtgg catcgtgacc                     40

<210> SEQ ID NO 140
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 140 tagggcgct gtcaagatgt gaatttatcc cgtgatatcg                      40

<210> SEQ ID NO 141
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 141
gataacaagc tgtgaattta tcacgtgaaa ctagccgttg                     40

<210> SEQ ID NO 142
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 142
ccgtacattt gttgaagaag cgcttatccc gatcctgtgc                     40

<210> SEQ ID NO 143
<211> LENGTH: 17
<212> TYPE: DNA
<213> ORGANISM: Artificial Sequence
<220> FEATURE:
<223> OTHER INFORMATION: Synthetic (aptamer sequence)

<400> SEQUENCE: 143
caagatgtga atttatc                                              17

<210> SEQ ID NO 144
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 144
aaacaggatg gtcaagatgt gaatttatcc ccgtgtgtcc                     40

<210> SEQ ID NO 145
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 145
tacaagatgt gaatttatcc ccgtgagtgg catcgtgacc                              40

<210> SEQ ID NO 146
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 146 tagggcgct gtcaagatgt gaatttatcc cgtgatatcg                              40

<210> SEQ ID NO 147
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 147
tcaagatgtg aatttatcac cgtggggcga aggacctgtg                              40

<210> SEQ ID NO 148
<211> LENGTH: 10
<212> TYPE: DNA
<213> ORGANISM: Artificial Sequence
<220> FEATURE:
<223> OTHER INFORMATION: Synthetic (aptamer sequence)

<400> SEQUENCE: 148
aatgtaagtc                                                              10

<210> SEQ ID NO 149
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 149
agaagttgga ggcaatgtaa gtcgcattaa tttttgccga                              40

<210> SEQ ID NO 150
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 150
tacaacagaa ggcgcggggc atgtaagtcc gttaattttt                              40

<210> SEQ ID NO 151
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 151
agatgtcctg gaggcggaat gtaagtccat taattttttcg                             40

<210> SEQ ID NO 152

```
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 152
atatgtggtg ctgaggggaa tgtaagtgca ttacattttt                              40

<210> SEQ ID NO 153
<211> LENGTH: 39
<212> TYPE: DNA
<213> ORGANISM: Artificial Sequence
<220> FEATURE:
<223> OTHER INFORMATION: Synthetic (aptamer sequence)

<400> SEQUENCE: 153
agggaatgta agtgggttac tttttcacga gagtggact                              39

<210> SEQ ID NO 154
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 154
caatgtaagt cgggttaatt tttgcatgtg gtgcgagtaa                              40

<210> SEQ ID NO 155
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 155
acaatgtaag tgaattagat ttttggcaac ggacatggtg                              40

<210> SEQ ID NO 156
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 156
caatgtaagt gcattaaatt tttgccaagg cctcagctgc                              40

<210> SEQ ID NO 157
<211> LENGTH: 9
<212> TYPE: DNA
<213> ORGANISM: Artificial Sequence
<220> FEATURE:
<223> OTHER INFORMATION: Synthetic (aptamer sequence)

<400> SEQUENCE: 157 aatgtaagt                                                                9

<210> SEQ ID NO 158
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 158
```
agaagttgga ggcaatgtaa gtcgcattaa tttttgccga                    40

<210> SEQ ID NO 159
<211> LENGTH: 39
<212> TYPE: DNA
<213> ORGANISM: Artificial Sequence
<220> FEATURE:
<223> OTHER INFORMATION: Synthetic (aptamer sequence)

<400> SEQUENCE: 159
aacgcaatgt aagttggtta atttttgcgt gagtcccgg                     39

<210> SEQ ID NO 160
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 160
agatgtcctg gaggcggaat gtaagtccat taatttttcg                    40

<210> SEQ ID NO 161
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 161
atatgtggtg ctgaggggaa tgtaagtgca ttacatttt                     40

<210> SEQ ID NO 162
<211> LENGTH: 39
<212> TYPE: DNA
<213> ORGANISM: Artificial Sequence
<220> FEATURE:
<223> OTHER INFORMATION: Synthetic (aptamer sequence)

<400> SEQUENCE: 162
agggaatgta agtgggttac tttttcacga gagtggact                     39

<210> SEQ ID NO 163
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 163
caatgtaagt cgggttaatt tttgcatgtg gtgcgagtaa                    40

<210> SEQ ID NO 164
<211> LENGTH: 40
<212> TYPE: DNA
<213> ORGANISM: Artificial Sequence
<220> FEATURE:
<223> OTHER INFORMATION: Synthetic (aptamer sequence)

<400> SEQUENCE: 164
acaatgtaag tgaattagat ttttggcaac ggacatggtg                    40

<210> SEQ ID NO 165
<211> LENGTH: 40
<212> TYPE: DNA

```
<213> ORGANISM: Artificial Sequence
<220> FEATURE:
<223> OTHER INFORMATION: Synthetic (aptamer sequence)

<400> SEQUENCE: 165
caatgtaagt gcattaaatt tttgccaagg cctcagctgc                              40

<210> SEQ ID NO 166
<211> LENGTH: 12
<212> TYPE: DNA
<213> ORGANISM: Artificial Sequence
<220> FEATURE:
<223> OTHER INFORMATION: Synthetic (primer)

<400> SEQUENCE: 166
tgtggtggtc gg                                                           12

<210> SEQ ID NO 167
<211> LENGTH: 14
<212> TYPE: DNA
<213> ORGANISM: Artificial Sequence
<220> FEATURE:
<223> OTHER INFORMATION: Synthetic (primer)

<400> SEQUENCE: 167
ccacaccacc agcc                                                         14
```

GLYPICAN-3 SPECIFIC APTAMER AND USE THEREOF

TECHNICAL FIELD

The present invention relates to a DNA aptamer specifically binding to Glypican-3 (GPC3) protein related with a hepatocellular carcinoma, treatment of cancers related to the Glypican-3 protein using the same, a composition for inhibiting a cancer and a composition for diagnosing a cancer comprising the same as an active ingredient.

RELATED ART

A hepatocellular carcinoma (HCC) is the seventh most common cancer worldwide, with approximately more than 1 million deaths annually due to HCC. Particularly in Korea, the incidence of HCC is high due to high prevalence of hepatitis B, and the death rate of HCC in Korea is 22.5 per 100,000 people, the second highest among all cancers. In particular, the death rate of HCC is high in the 30-50 s, where economic activity is intense, so the loss income is 2.531 trillion won, which is the number 1 among cancers and is superiorly high loss to gastric cancer (1.5760 trillion won) or lung cancer (1.1320 trillion won). The 5-year survival rate of HCC in Korea is 23.3%, which is the third worst after pancreatic cancer and lung cancer.

Early hepatocellular carcinomas of less than 3 cm can be relatively safely treated by not only surgical resection but also percutaneous alcohol injection, high-frequency heat treatment, etc., and long-term survival is good, but successful treatment is not expected in advanced stages. Therefore, early diagnosis is essential to improve the prognosis of patients with hepatocellular carcinomas. However, there are limits of diagnosing atypical HCC early by current imaging studies such as CT/MRI etc. In order to increase the diagnostic accuracy and sensitivity/specificity of HCC including atypical HCC, the necessity of HCC specific contrast agent, which can be displayed on imaging studies such as CT or MRI, etc. emerged.

Currently the standard treatment for advanced HCC is oral anticancer targeted agent, sorafenib, but the increase in survival time is only about 2-3 months, so it is not enough to meet the expectation. In addition, it is a representative limit that even a HCC-targeted agent acts on mucous cells of skin cells and gastrointestinal tract, causing various severe side effects such as hand-foot syndrome that skins of hand and foot are peeled off, waterly diarrhea, abdominal pain, etc. It is interpreted as a problem occurred because the protein targeted by sorafenib exists in other normal cells. Therefore, there is a need for a more elaborate, specific and stable targeted agent capable of acting on a protein specifically present in hepatocellular carcinoma cells, but a targeted agent superior to sorapenib has not been developed until now.

In the present invention, an aptamer that specifically binds t Glypican-3 (GPC3) surface protein over-expressed in hepatocellular carcinoma cell membrane was developed. The biological mechanism of GPC3 is not precisely known, but it has received attention as a new therapeutic target due to specificity to hepatocellular carcinoma cell, and various kinds of monoclonal antibodies to GPC3 (MDX-1414, HN3, GC33, YP7) has been developed worldwide, and are in preclinical/clinical trials. The aptamers selectively binding to GPC3 developed in the present invention are expected to be more effectively used for treatment and diagnosis of hepatocellular carcinoma.

Technical Problem

An object of the present invention is to provide an aptamer specifically binding to a hepatocellular carcinoma-related Glypican-3 protein, a pharmaceutical composition and a composition for diagnosis comprising the same, and a method for providing information to diagnosis of hepatocellular carcinoma or hepatocellular carcinoma metastasis using the same.

Technical Solution

Hence, the present inventors developed a Glypican-3 specific binding aptamer that specifically binds to a Glypican-3 protein, in order to achieve the above object.

The aptamer specifically binding to Glypican-3 can be more effectively applied to treatment and diagnosis of a hepatocellular carcinoma.

Hereinafter, the present invention will be explained in more detail.

An embodiment of the present invention relates to Glypican-3 (GPC3) specific aptamer specifically binding to a Glypican-3 protein and comprising deoxyuridine (dU) including a hydrophobic functional group substituted at 5-position of a pyrimidine group. The modification of deoxyuridine (dU) can be carried out by introducing a hydrophobic functional group to 5-position of pyrimidine group of deoxyuridine. Preferably, the hydrophobic functional group can be a benzyl or a naphthyl group. The aptamer can be isolated from a living body or non-naturally produced, for example, produced recombinantly or synthetically.

Another embodiment of the present invention relates to Glypican-3 specific aptamer comprising a core sequence of one or more sequences selected from the group consisting of SEQ ID NO: 1 to SEQ ID NO: 44.

The sequences of SEQ ID NOs: 1 to 44 include one or more primer sequences and core sequences, and their sequences are shown in the following table 1 and table 2.

TABLE 1

| Name | (5'primer-17mer) (SEQ ID NO: 45) | core sequence (number of bases, SEQ ID NO.) | (3'primer-17mer) (SEQ ID NO: 46) |
|---|---|---|---|
| s003-H10010-T7_B08 | 5'-TCAGCCGCCAGCCAGTTC- | nnnCCGCnGnAnnnAGCAGnGAGCGnnnAnnCGCCnCAAA(40, SEQ ID NO: 1) | GACCAGAGCACCACAGAG-3' |
| s003-H10022-T7_F09 | 5'-TCAGCCGCCAGCCAGTTC- | CnCGnnGACnnAnCCACCnnCAGnAGGGnCnGAGCGnCG(39, SEQ ID NO: 2) | GACCAGAGCACCACAGAG-3' |

TABLE 1-continued

| Name | (5'primer-17mer) (SEQ ID NO: 45) | core sequence (number of bases, SEQ ID NO.) | (3'primer-17mer) (SEQ ID NO: 46) |
|---|---|---|---|
| s003-H10011-T7_C08 | 5'-TCAGCCGCCAGCCAGTTC- | nAnGAnnnGGCAGAnnAAACnnCCGCAGCAGnnnnCCCGG(40, SEQ ID NO: 3) | -GACCAGAGCACCACAGAG-3' |
| s003-H10012-T7_D08 | 5'-TCAGCCGCCAGCCAGTTC- | CGCAGnCCGnnGACnnAnnnGCACCGnGnGAnnGnnCAGn(40, SEQ ID NO: 4) | -GACCAGAGCACCACAGAG-3' |
| s003-H10019-T7_C09 | 5'-TCAGCCGCCAGCCAGTTC- | GCGnnGACnnAnCAnCCCCCAGnCGGCnnGCAGGCCGGCn(40, SEQ ID NO: 5) | -GACCAGAGCACCACAGAG-3' |
| s003-H10026-T7_B10 | 5'-TCAGCCGCCAGCCAGTTC- | GnAAAnAGnGnGnGAnnnGnGnAAnCAGnnnACAGACGGG(40, SEQ ID NO: 6) | -GACCAGAGCACCACAGAG-3' |
| s003-H10001-T7_A07 | 5'-TCAGCCGCCAGCCAGTTC- | GnnGACnnGAnnnGGGACnnGnnCAGnAACGCAGCCnnGAC(41, SEQ ID NO: 7) | -GACCAGAGCACCACAGAG-3' |
| s003-H10004-T7_D07 | 5'-TCAGCCGCCAGCCAGTTC- | nCGGCnGGnCnGCGnGnGnnGnCGGCAnGnAGAnCnCGCG(40, SEQ ID NO: 8) | -GACCAGAGCACCACAGAG-3' |
| s003-H10038-T7_D07 | 5'-TCAGCCGCCAGCCAGTTC- | AGnGCnCnAnnAnGCCGGGCnAnnnAnnCCCGGGGCGGnn(40, SEQ ID NO: 9) | -GACCAGAGCACCACAGAG-3' |
| s003-H10006-T7_D07 | 5'-TCAGCCGCCAGCCAGTTC- | nCAGCnnCCGnnGACnnAnAnCCCnnCAGnGAAGCCCnCn(40, SEQ ID NO: 10) | -GACCAGAGCACCACAGAG-3' |
| s003-H10002-T7_D07 | 5'-TCAGCCGCCAGCCAGTTC- | GGGGAGnnAACGCGnnGAAnnAnGnCCCnnCAGnCGGCAC(40, SEQ ID NO: 11) | -GACCAGAGCACCACAGAG-3' |
| s003-H10014-T7_D07 | 5'-TCAGCCGCCAGCCAGTTC- | GGGAAGnGAAnGCGnnGAAnnAnGnCCCnnCAGnCAnCAC(40, SEQ ID NO: 12) | -GACCAGAGCACCACAGAG-3' |
| s003-H10033-T7_D07 | 5'-TCAGCCGCCAGCCAGTTC- | GCnnCnnCGAnnGAAnnnAAGAnAnGCGnCCnCAGACACA(40, SEQ ID NO: 13) | -GACCAGAGCACCACAGAG-3' |
| s003-H10020-T7_D07 | 5'-TCAGCCGCCAGCCAGTTC- | nAnGnnnnGGAGGAnnAAAnCCCGCGAnnnnCAGAGnGCCCC(42, SEQ ID NO: 14) | -GACCAGAGCACCACAGAG-3' |

TABLE 2

| Name | (5'primer-17mer) (SEQ ID NO: 47) | core sequence (number of bases, SEQ ID NO.) | (3'primer-17mer) (SEQ ID NO: 48) |
|---|---|---|---|
| S033-C1-01-M13-20R_A01 | 5'-CGAGCGTCCTGCCTTTG- | GnAAnAAAnAGnGACnGAnnnnGnGnnCCGnnnACACCAA(40, SEQ ID NO: 15) | -CACCGACAGCCACCCAG-3' |

TABLE 2-continued

| Name | (5'primer-17mer) (SEQ ID NO: 47) | core sequence (number of bases, SEQ ID NO.) | (3'primer-17mer) (SEQ ID NO: 48) |
|---|---|---|---|
| S033-C1-10-M13-20R_B02 | 5'-CGAGCGTCCTGCCTTTG- | ACCAnAGCACGnAACGGAGCnnGCGCCCAACCGCAnACAC(40, SEQ ID NO: 16) | CACCGACAGCCACCCAG-3' |
| S033-C1-11-M13-20R_C02 | 5'-CGAGCGTCCTGCCTTTG- | AnGnGAnAAAnAGnAAnnGAnnnnGnACnCAGnnnACAnA(40, SEQ ID NO: 17) | CACCGACAGCCACCCAG-3' |
| S033-C1-12-M13-20R_D02 | 5'-CGAGCGTCCTGCCTTTG- | GAnCAnAAAnAGnnnCnGAnnnnGnAGnCCGnnnACGAGA(40, SEQ ID NO: 18) | CACCGACAGCCACCCAG-3' |
| S033-C1-17-M13-20R_A03 | 5'-CGAGCGTCCTGCCTTTG- | GGCACCnCCCCnnGACnnAnnCCACCnnCAGnGGGGnGC(40, SEQ ID NO: 19) | CACCGACAGCCACCCAG-3' |
| S033-C1-02-M13-20R_B01 | 5'-CGAGCGTCCTGCCTTTG- | ACGnGCnnnnnnnAAnGnACCGGGnnnnGnCCGGGCAGCGA(40, SEQ ID NO: 20) | CACCGACAGCCACCCAG-3' |
| S033-C1-25-M13-20R_A04 | 5'-CGAGCGTCCTGCCTTTG- | nACGnGCCGnnGACnnAnAnCCCnCAGnGCnCCnnCCCnC(40, SEQ ID NO: 21) | CACCGACAGCCACCCAG-3' |
| S033-C1-37-M13-20R_E05 | 5'-CGAGCGTCCTGCCTTTG- | CGnCAGAGCnGGnnGCGGnGCCCGGnAnnnGCnCCGGCGCC(41, SEQ ID NO: 22) | CACCGACAGCCACCCAG-3' |
| S033-C1-46-M13-20R_E05 | 5'-CGAGCGTCCTGCCTTTG- | nAAAnAGnGnCnAAnnnnGnAnCGnnnAnCGCnAGAAGCn(40, SEQ ID NO: 23) | CACCGACAGCCACCCAG-3' |
| S033-C1-16-M13-20R_E05 | 5'-CGAGCGTCCTGCCTTTG- | ACGAAAAnCnAnACnnnCAAGGGGnnnnGnACnAAnCCCG(40, SEQ ID NO: 24) | CACCGACAGCCACCCAG-3' |
| S033-C1-30-M13-20R_E05 | 5'-CGAGCGTCCTGCCTTTG- | AnGGnGGCnAACnnGGCCGnnGACnnAnAnCCCnCAGnG(39, SEQ ID NO: 25) | CACCGACAGCCACCCAG-3' |
| S033-D1-01-M13-20R_A07 | 5'-CGAGCGTCCTGCCTTTG- | CAACGGCmAGmmmCACGmGAAAAmmCACAGCmmGmmAmC(40, SEQ ID NO: 26) | CACCGACAGCCACCCAG-3' |
| S033-D1-10-M13-20R_B08 | 5'-CGAGCGTCCTGCCTTTG- | mACAAGAmGmGAAmmmAmCCCCGmGAGmGGCAmCGmGACC(40, SEQ ID NO: 27) | CACCGACAGCCACCCAG-3' |
| S033-D1-12-M13-20R_D08 | 5'-CGAGCGTCCTGCCTTTG- | GCAmAmGAGGGmmAGGCmAGCCAmCmmmGGGGCAGCAGGA(40, SEQ ID NO: 28) | CACCGACAGCCACCCAG-3' |
| S033-D1-19-M13-20R_C09 | 5'-CGAGCGTCCTGCCTTTG- | mmmGGGGmGGmAGGACACGGmGAmAAAGAmCmGGCCCGC(40, SEQ ID NO: 29) | CACCGACAGCCACCCAG-3' |
| S033-D1-32-M13-20R_H10 | 5'-CGAGCGTCCTGCCTTTG- | CAAmGmAAGmGCAmmAAAmmmmmGCCAAGGCCmCAGCmGC(40, SEQ ID NO: 30) | CACCGACAGCCACCCAG-3' |

TABLE 2-continued

| Name | (5'primer-17mer) (SEQ ID NO: 47) | core sequence (number of bases, SEQ ID NO.) | (3'primer-17mer) (SEQ ID NO: 48) |
|---|---|---|---|
| S033-D1-07-M13-20R_G07 | 5'-CGAGCGTCCTGCCTTTG- | mCAAGAmGmGAAmmmAmCACCGmGGGGCGAAGGACCmGmG(40, SEQ ID NO: 31) | CACCGACAGCCACCCAG-3' |
| S033-D1-02-M13-20R_G07 | 5'-CGAGCGTCCTGCCTTTG- | GGACACACGGGGAmAAAmmCACAmCmmGACCAmCCmGmmm(40, SEQ ID NO: 32) | CACCGACAGCCACCCAG-3' |
| S033-D1-28-M13-20R_G07 | 5'-CGAGCGTCCTGCCTTTG- | GCACAGGAmCGGGAmAAGCGCmmCmmCAACAAAmGmACGG(40, SEQ ID NO: 33) | CACCGACAGCCACCCAG-3' |
| S033-D1-44-M13-20R_G07 | 5'-CGAGCGTCCTGCCTTTG- | mCGGCAAAAAmmAAmGCGACmmACAmmGCCmCCAACmmCm(40, SEQ ID NO: 34) | CACCGACAGCCACCCAG-3' |
| S033-D1-46-M13-20R_G07 | 5'-CGAGCGTCCTGCCTTTG- | AACGCAAmGmAAGmmGGmmAAmmmmmGCGmGAGmCCCGG(39, SEQ ID NO: 35) | CACCGACAGCCACCCAG-3' |
| S033-D1-27-M13-20R_G07 | 5'-CGAGCGTCCTGCCTTTG- | CAmGmAAGmGAAmmAAmmmmmmGCGAAGGGCAmGGAAAGGC(40, SEQ ID NO: 36) | CACCGACAGCCACCCAG-3' |
| S033-D1-37-M13-20R_G07 | 5'-CGAGCGTCCTGCCTTTG- | GmCmGGmCCmAmCGmGmGCGGmGCCGmGACmACAGAAmmm(40, SEQ ID NO: 37) | CACCGACAGCCACCCAG-3' |
| S033-D1-22-M13-20R_G07 | 5'-CGAGCGTCCTGCCTTTG- | AmAGGGmGmGAmCGCAGAGGGmmAmCAAAGAGGACAmGGA(40, SEQ ID NO: 38) | CACCGACAGCCACCCAG-3' |
| S033-D1-31-M13-20R_G07 | 5'-CGAGCGTCCTGCCTTTG- | mGCmmACmmmmAmGACACGmCCCGCACAAAAGGCCmAGmG(40, SEQ ID NO: 39) | CACCGACAGCCACCCAG-3' |
| S033-D1-18-M13-20R_G07 | 5'-CGAGCGTCCTGCCTTTG- | mAmGCCmmmmGACmACACCCmGAmCCmACCCACCACCmCA(40, SEQ ID NO: 40) | CACCGACAGCCACCCAG-3' |
| S033-D1-42-M13-20R_G07 | 5'-CGAGCGTCCTGCCTTTG- | GmGGGCAmGmAAGmAGGAmmAAmmmmmGAACCACCAGmAG(40, SEQ ID NO: 41) | CACCGACAGCCACCCAG-3' |
| S033-D1-45-M13-20R_G07 | 5'-CGAGCGTCCTGCCTTTG- | CmCCAmmGmmmAmAmGAmAAGGCAGGCAAGGGGCCCACCGGA(42, SEQ ID NO: 42) | CACCGACAGCCACCCAG-3' |

TABLE 2-continued

| Name | (5'primer-17mer) (SEQ ID NO: 47) | core sequence (number of bases, SEQ ID NO.) | (3'primer-17mer) (SEQ ID NO: 48) |
|---|---|---|---|
| S033-D1-08-M13-20R_H07 | 5'-CGAGCGTCCTGCCTTTG- | CCCCAmGmmAAAmGmmGGCGmmCmGCGGAmmmCGGCGAmA(40, SEQ ID NO: 43) | CACCGACAGCCACCCAG-3' |
| S033-D1-16-M13-20R_H08 | 5'-CGAGCGTCCTGCCTTTG- | mGmGGCAACmAGGCmGGCmmACGAAAGCAGGmAGCCGAGG(40, SEQ ID NO: 44) | CACCGACAGCCACCCAG-3' |

In the table 1 and table 2, the nucleotide represented as n is a nucleotide including a benzyl group introduced to 5-position of pyrimidine group of deoxyuridine (BzdU), as shown in chemical formula 1. The nucleotide represented as m is a nucleotide including a naphthyl group introduced to 5-position of pyrimidine group of deoxyuridine (NapdU), as shown in chemical formula 2.

[Chemical formula 1]

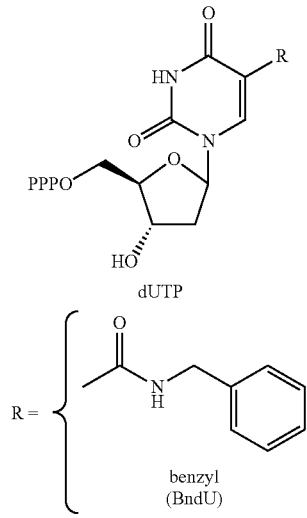

benzyl
(BndU)

[Chemical formula 2]

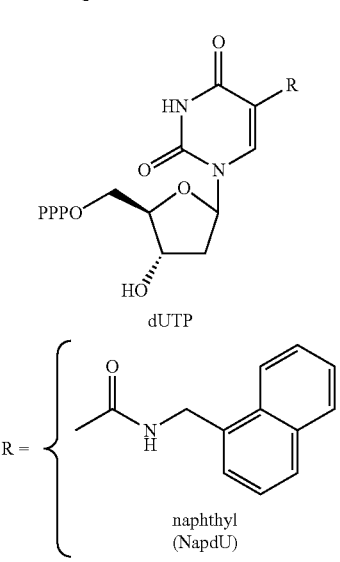

naphthyl
(NapdU)

In the aptamer, one or more aptamer selected from the group consisting of SEQ ID NO: 1 to SEQ ID NO: 44 can further comprise a primer sequence to 5' end, 3' end, or both ends of a core sequence. The primer sequence can be one or more selected from the group consisting of SEQ ID NO: 45 to SEQ ID NO: 48.

Preferably, one or more primer sequences selected from the group consisting of SEQ ID NO: 45 and SEQ ID NO: 47 can be connected to 5' end of the core sequence, and one or more primer sequences selected from the group consisting of SEQ ID NO: 46 and SEQ ID NO: 48 can be connected to 3' end of the core sequence.

More preferably, the aptamer of present invention can comprise the primer sequence of SEQ ID NO: 45 in 5' end and the primer sequence of SEQ ID NO: 46 in 3' end of the core sequences that is one or more selected from the group consisting of SEQ ID NOs: 1 to 14. In addition, the aptamer of the present invention can comprise the primer sequence of SEQ ID NO: 47 in 5' end and the primer sequence of SEQ ID NO: 48 in 3' end of the core sequence that is one or more selected from the group consisting of SEQ ID NOs: 15 to 44.

A preferable embodiment of aptamer according to the present invention is Glypican-3 specific aptamer comprising one or more sequences selected from the group consisting of SEQ ID NOs: 1 to 44.

Glypican-3 is a surface protein over-expressed in a cell membrane of a hepatocellular carcinoma cell. The aptamer of the present invention has specific and high binding activity to Glypican-3 protein. When the aptamer of the present invention binds the Glypican-3 protein, the dissociation constant (Kd) value is a range of 0.1 to 35 nM, preferably 0.1 to 4.5 nM, more preferably 0.1 to 1.0 nM.

In addition, the aptamer of the present invention inactivates Yap protein. Yap protein is one kind of oncogenes, and has been known as an intracellular downstream signal factor of hepatocellular carcinoma specific membrane protein. Yap protein has been known that it cannot act anymore when it is decomposed by phosphorylation. The aptamer of the present invention increases the phosphorylated Yap proteins in a cell and inactivates Yap protein, thereby inhibiting growth of hepatocellular carcinoma cells.

The aptamer, in order to enhance stability in serum or regulate renal clearance, can modify 5' end, 3' end, the middle or both ends. The modification of aptamer can be performed by combining one or more selected from the group consisting of PEG (polyethylene glycol), idT (inverted deoxythymidine), LNA (Locked Nucleic Acid), 2'-methoxy nucleoside, 2'-amino nucleoside, 2'F-nucleoside, an amine linker, a thiol linker, and a cholesterol, etc. to 5' end, 3' end, the middle or both ends of aptamer. The idT (inverted deoxythymidine) is generally one of molecules used to prevent decomposition of an aptamer by nuclease, because the aptamer has low tolerance to the nuclease. The nucleotide monomer unit forms a chain by binding to 3'-OH of the preceding unit and 5'-OH of the next unit, but idT binds 3'-OH of the next unit to 3'-OH of the preceding unit, and thereby 5'-OH is exposed, not 3'-OH. The artificial modification in the idT prevents the decomposition caused by 3' exonuclease that is one kind of nucleases.

The aptamer according to the present invention can further comprise a fluorescent molecule, a toxin or a control reagent. In a preferable embodiment, the aptamer can be labeled with F18 or P32 as a radioactive isotope.

A DNA aptamer is composed of short nucleic acid chain and has a smaller molecular size than antibody drugs. Therefore, it can be chemically synthesized and modified for being applied to a living body easily, and it has excellent penetrating ability into tumor tissues. DNA aptamer has various advantages as an anticancer molecule.

Since a natural oligonucleotide is sensitive to hydrolysis by a nuclease, it is a main point to stabilize a phosphate backbone in biomedical application of a DNA aptamer. If a DNA aptamer is modified by using neutral groups such as methyl phosphonate and phosphoramidate, the modified aptamer has increased resistance to a nuclease, but lower binding affinity compared to non-modified oligonucleotide. In order to increase binding affinity and reduce off-rate, SELEX was performed using the nucleotides modified with various functional groups. The result data show the DNA aptamer modified by a benzyl group has high affinity to periostin (1 nM) and minimized cross-reaction. Because of potential conformational differences between purified proteins and endogenous proteins in a living body, the isolated aptamers obtained for the purified proteins cannot bind to their targeted protein always, when being applied in a living body. Thus, it is necessary to integrate in vivo conditions to a screening process, in order to identify an aptamer having an activity in a living body.

Compared to a previously developed antibody to GPC3, the DNA aptamer of the present invention show more rapid tumor uptake, more rapid blood removal and more sustained tumor retention, and thereby making it possible to significantly image as a higher ratio of tumor to blood. In addition, an aptamer having the targets such as a toxin, complicated protein complex or glycoprotein complex can be prepared, but an antibody for the targets cannot be prepared easily.

In particular, because of high stability, an aptamer can be stored or delivered in a room temperature, can maintain its function after sterilization, and can be regenerated in a short time if denatured. Thus, in case that an aptamer is used as a diagnostic marker or drugosis for long-time or repeated use, it has higher applicability than an antibody. In addition, the production of aptamer can be performed with very little batch-to-batch variation and easy purification for high purity due to high homogeneity of aptamer. The immunorejection responses in a living body hardly occur.

Another embodiment of the present invention provides a pharmaceutical composition for treating a hepatocellular carcinoma, preventing a hepatocellular carcinoma, or inhibiting hepatocellular carcinoma metastasis, comprising an aptamer which specifically binds to Glypican-3 (GPC3) protein and includes deoxyuridine (dU) having a hydrophobic functional group substituted at 5-position of a pyrimidine group; or a method of use an aptamer which specifically binds to Glypican-3 (GPC3) protein and includes deoxyuridine (dU) having a hydrophobic functional group substituted at 5-position of a pyrimidine group, for treating a hepatocellular carcinoma, preventing a hepatocellular carcinoma, or inhibiting hepatocellular carcinoma metastasis.

The aptamer as described above can be applied to the composition.

The aptamer according to the present invention can be specifically or selectively used for treatment, prevention and/or metastasis inhibition of a hepatocellular carcinoma without side effects caused by the aptamer action in a normal cell, as the aptamer specifically binds to GPC3 protein over-expressed in a hepatocellular carcinoma cellular membrane.

The aptamer according to the present invention inhibits adhesion, proliferation, migration and invasion of a hepatocellular carcinoma cell, and preferably, it shows a notable effect for inhibiting growth of a hepatocellular carcinoma cell.

The pharmaceutical composition can further comprise a pharmaceutically acceptable carrier.

The Glypican-3 specific aptamer or the pharmaceutical composition comprising the same can be formulated into various oral administration forms or parenteral administration forms. For example, it can be any form of oral administration such as tablets, pills, hard. soft capsules, liquids, suspensions, emulsions, syrups, granules, elixirs, etc. Such formulations for oral administration can comprises a pharmaceutically acceptable carrier like diluents such as lactose, dextrose, sucrose, mannitol, sorbitol, cellulose and/or glycine, lubricants such as silica, talc, stearic acid and its magnesium or calcium salt and/or polyethylene glycol, etc., in addition to the active ingredient, depending on the typical configuration of each formulation.

In addition, when the formulation for oral administration is a tablet, a binder such as magnesium aluminum silicate, starch paste, gelatin, tragacanth, methyl cellulose, sodium carboxymethyl cellulose and/or polyvinyl pyrrolidine, etc. can be comprised, and in some cases, a disintergrating agent such as starch, agar, alginic acid, or its sodium salt, a boiling mixture and/or an absorbent, a coloring agent, a flavoring agent, or a sweetening agent, etc. can be comprised.

In addition, when the Glypican-3 specific aptamer or the pharmaceutical composition comprising the same is formulated in a parenteral administration form, it can be administered in a parenteral administration route such as a subcutaneous injection, an intravenous injection, an intramuscular injection, or an intrathoracic injection, etc. Then, in order to formulate as the parenteral administration form, the pharmaceutical composition can be produced as liquids or suspensions as an active ingredient, that is the aptamer is mixed with a stabilizer or a buffer together in water, and such liquids or suspensions can be produced in a unit administration form of an ample or a vial.

In addition, the pharmaceutical composition can be sterilized or further comprise adjuvants such as preservatives, stabilizers, wettable powders or emulsifying accelerators, salts for controlling osmotic pressure and/or buffers, etc., and it can further comprise other therapeutically useful substances, and it can be formulated according to conventional methods of mixing, granulation or coating.

In addition, the term "pharmaceutically effective dose" means the amount of an active ingredient showing a desired effect, that is, an effect of prevention and/or treatment of hepatocellular carcinoma, or inhibition of hepatocellular carcinoma metastasis. The active ingredient, that is, Glypican-3 specific aptamer can be comprised in the pharmaceutical composition in an effective dose of 0.1 to 500 mg/kg (body weight), preferably 0.5 to 100 mg/kg (body weight) a day, and such pharmaceutical composition can be administered through an oral or parenteral route once a day or divided into twice or more times.

A subject of administration of Glypican-3 specific aptamer or the pharmaceutical composition comprising the same of the present invention can be a mammal including a human, preferably a rodent, or a human.

In addition, as another embodiment of the present invention, since Glypican-3 protein is over-expressed in a patient of a hepatocellular carcinoma and cancer metastasis, the Glypican-3 specific aptamer can be used as a composition for diagnosing a hepatocellular carcinoma and/or hepatocellular carcinoma metastasis.

Another embodiment provides a method for treating a cancer and/or inhibiting cancer metastasis comprising a step of administering a pharmaceutically effective dose of the Glypican-3 specific aptamer to a patient who needs cancer treatment and/or cancer metastasis inhibition. The method can further comprise a step of confirming a patient who needs cancer treatment and/or cancer metastasis inhibition before the administration step.

As another aspect, the present invention comprises a method for providing information to diagnosis of a hepatocellular carcinoma or hepatocellular carcinoma metastasis comprising a step of reacting the Glypican-3 specific aptamer to a biological sample of a patient; a step of measuring the binding degree of the aptamer and Glypican-3 protein in the sample; and a step of determining the patient as a hepatocellular carcinoma patient when the binding degree of the aptamer and Glypican-3 protein in the sample is higher than that of a normal sample.

The aptamer as described above can be applied to the method.

The method can further comprise a step of measuring the binding degree of the Glypican-3 specific aptamer in a normal cell.

The patient can be a mammal including a human, preferably a rodent, or a human, and means a subject to determine whether a cancer develops or metastasized.

The normal sample can be a mammal including a human, preferably a rodent, or a human, and means a biological sample obtained from an individual without a hepatocellular carcinoma or hepatocellular carcinoma metastasis that will provide information to diagnosis.

The biological sample can be a cell, a tissue, blood, body fluids, saliva, etc. isolated from a mammalian organism excluding a human, a mammal including a human.

The step of measuring the binding degree of Glypican-3 specific aptamer in the biological sample can be performed by using a DNA aptamer binding measuring techniques commonly used in the related art, and for example, a method of measuring fluorescence or radioactive intensities by labeling a fluorescent or radioactive substance or binding biotin to the aptamer end, or observing by imaging, etc. can be used, but not limited thereto.

Thus, when presence or over-expression of Glypican-3 protein in a sample is confirmed using the aptamer, significantly excellent sensitivity shows than detection using an existing monoclonal antibody.

Advantageous Effects

The Glypican-3 protein specific aptamer of the present invention can be used usefully as uses of an anticancer agent and/or cancer diagnosis by inhibiting adhesion, proliferation, migration and invasion of hepatocellular carcinoma cells.

BRIEF DESCRIPTION OF THE DRAWINGS

FIGS. 2a and 2b are results of analysis of sequences of GPC3 aptamer after primary SELEX, and FIGS. 2c to 2f are those after secondary SELEX.

FIG. 3a and FIG. 3b show results of measuring a binding activity of GPC3 aptamer discovered after primary or secondary SELEX respectively.

FIG. 5a and FIG. 5b are results of verifying a binding activity and selectivity of GPC3 aptamer discovered after primary or secondary SELEX respectively to a hepatocellular carcinoma cell line.

FIG. 8 shows a change of protein expression after administration of GPC3 aptamer.

FIG. 9 shows a change of phosphorylated Yap expression after administration of GPC3 aptamer.

FIG. 10 briefly shows a mechanism of inhibiting a hepatocellular carcinoma cell growth of GPC3 aptamer.

FIG. 11 shows specific binding to a mouse hepatocellular carcinoma tissue of GPC3 aptamer labeled with F-18.

FIG. 12 is a result of confirming binding of Cy5-anti-primer and GPC3 aptamer through agarose gel loading.

FIG. 13a is a confocal image result of confirming specific binding of Cy5-anti-primer-combined GPC3 aptamer to hepatocellular carcinoma cell line SNU-475, and FIG. 13b is a confocal image result of confirming specific binding of Cy5-anti-primer to hepatocellular carcinoma cell line SNU-475.

FIG. 14a is a confocal image result of confirming specific binding of Cy5-anti-primer-combined GPC3 aptamer to control cell line CHO, and FIG. 14b is a confocal image result of confirming specific binding of Cy5-anti-primer to control cell line SNU-475.

FIG. 15 shows the biodistribution of F-18 labeled GPC3 aptamer by mouse organs.

BEST MODE FOR CARRYING OUT THE INVENTION

Hereinafter, the present invention will be described in detail with examples. However, the following examples are illustrative purposes only, and the present invention is not limited by the following examples.

Figure 1:
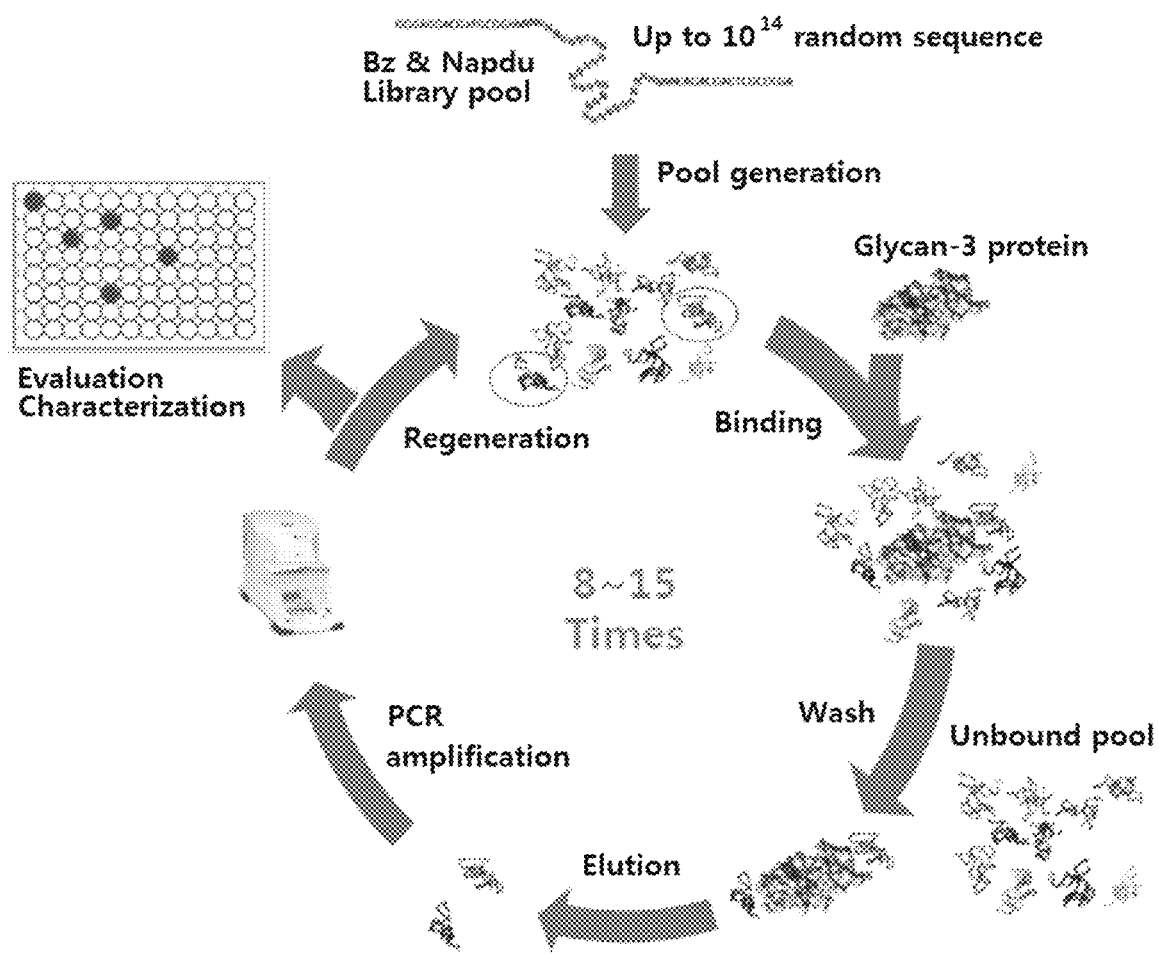
FIG. 1 is a schematized process of discovering an aptamer specifically binding a Glypican-3 protein using SELEX.

Example 1. Discovery of Glypican-3 (GPC3) Specific Binding Aptamer 1.1 Discovery of Glypican-3 Specific Binding Aptamer Through SELEX A novel Glypican-3 specific aptamer having selectively high binding activity to Glypican-3 protein was investigated using SELEX (Systematic Evolution of Ligands by Exponential Enrichment) technique after synthesizing 1014 numbers of BzdU library and NapdU library. The process is schematically shown in FIG. 1.

Aptamers having high binding activity to GPC3 was screened by analyzing sequences of candidate aptamers found by the discovery process and classifying into multicopy, family 14 kinds as a result of the primary SELEX and 30 kinds as a result of the secondary SELEX were discovered. Sequence analysis results of discovered aptamers were shown in FIGS. 2a and 2b (primary SELEX, the above table 1) and FIGS. 2c to 2f (secondary SELEX, the above table 2).

1.2 Evaluation of Binding Activity of Discovered Aptamers

Figure 4A:
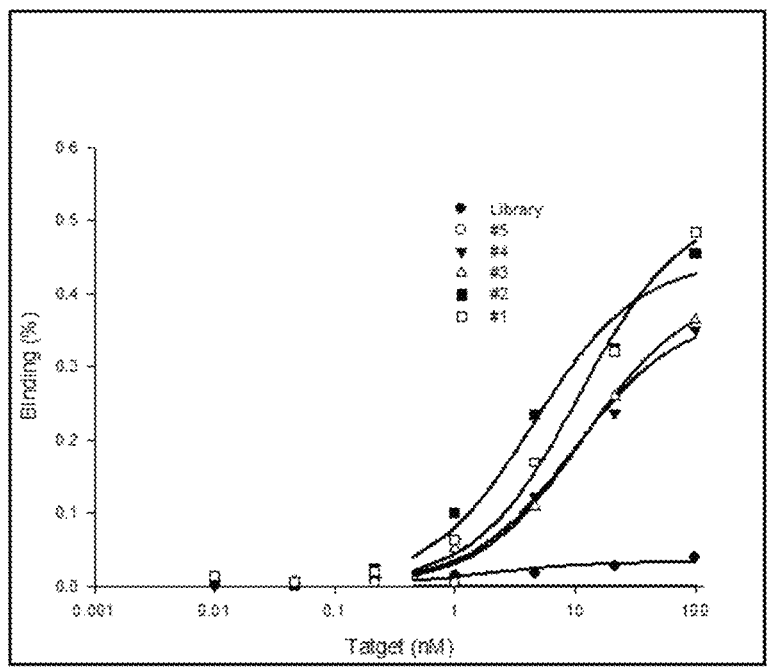
FIG. 4a and FIG. 4b show a dissociation constant (Kd) value of GPC3 aptamer discovered after primary or secondary SELEX respectively.
Figure 4B:
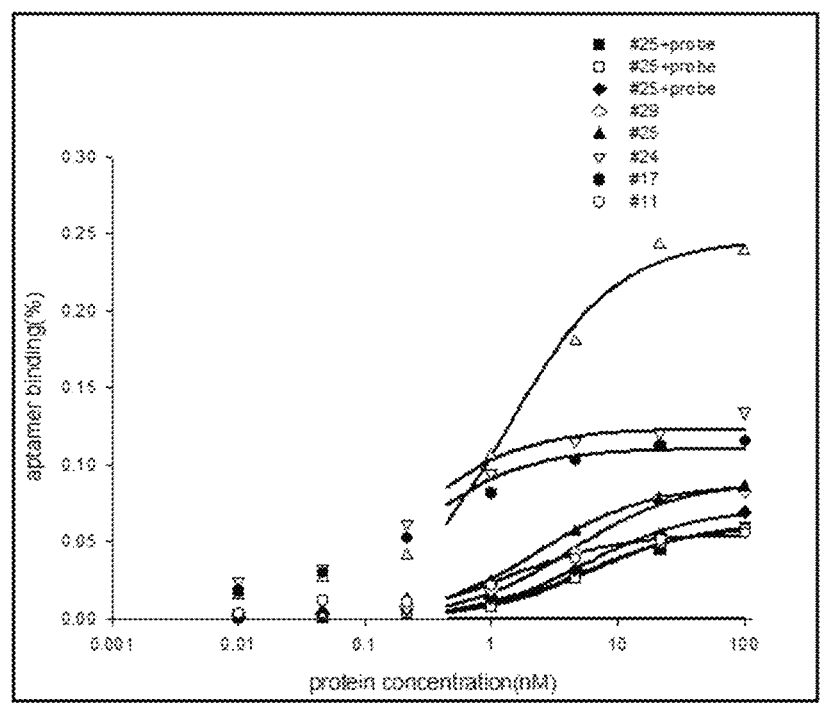

The binding activity of aptamers to the targeted protein, Glypican-3 protein was measured. Glypican-3 proteins were prepared at various concentrations and aptamers labeled with radioactive isotope ($P^{32}$) were mixed, thereby measuring the amount of GPC3 aptamers which bound to the protein using a radiation map. The concentration of targeted protein (Glypican-3) and the amount of bound GPC3 aptamers were analyzed, thereby determining an aptamer dissociation constant (Kd) value. The analysis process was briefly shown in FIG. 3a and FIG. 3b, and the measured aptamer dissociation constant value was shown in FIG. 4a and FIG. 4b.

The Kd value of the GPC3 aptamer showing the highest binding activity to Glypican-3 protein after the primary SELEX was 4.5 nM (Bmax=0.4456), and the Kd value of the GPC3 aptamer showing the highest binding activity to Glypican-3 protein after the secondary SELEX was 0.19 nM (Bmax=0.12).

Figure 5B:
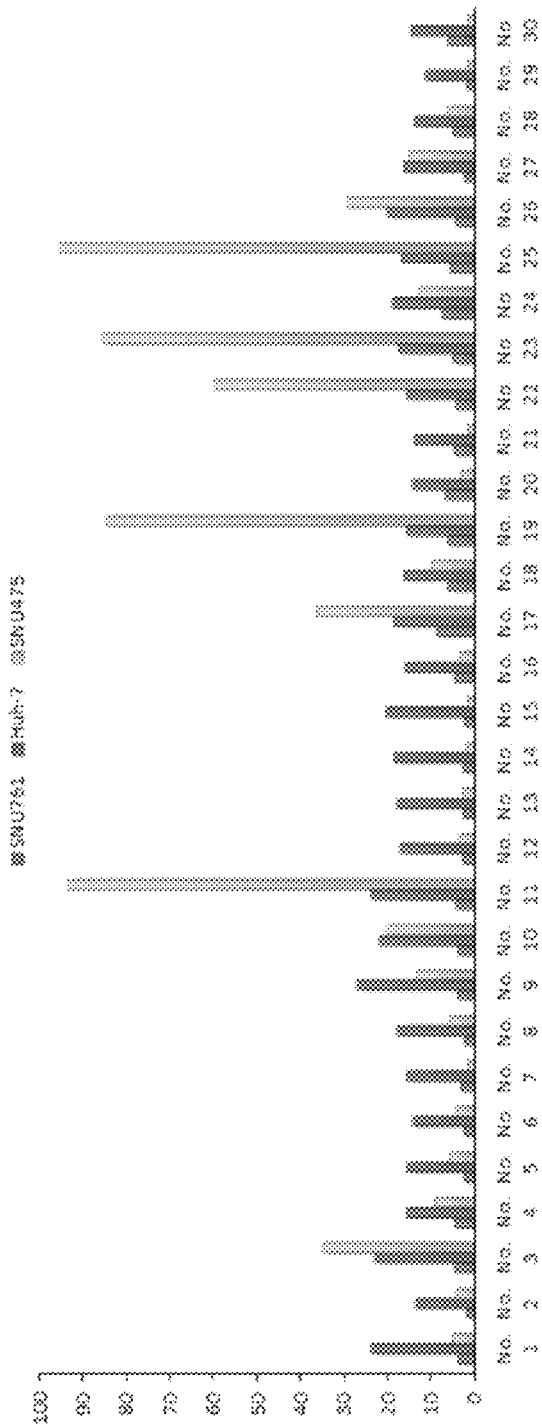

Example 2. Evaluation of In Vitro Efficacy of Glypican-3 (GPC3) Specific Binding Aptamer 2.1 Confirmation of Selective Binding Activity of GPC3 Aptamer in a Hepatocellular Carcinoma Cell Line Using FACS Method The binding activity of FITC-labeled GPC3 aptamers (primary SELEX 14 kinds, secondary SELEX 30 kinds) to a hepatocellular carcinoma cell line was confirmed using FACS method. The binding activity to a normal hepatic stellate cell line LX-2 and hepatocellular carcinoma cell lines Huh-7, SNU761, SNU475, SH3, H17 was confirmed, and the GPC3 aptamer showing high binding activity to the hepatocellular carcinoma cell lines was screened. The result of measuring the binding activity was shown in FIG. 5a and FIG. 5b.

Figure 6A:
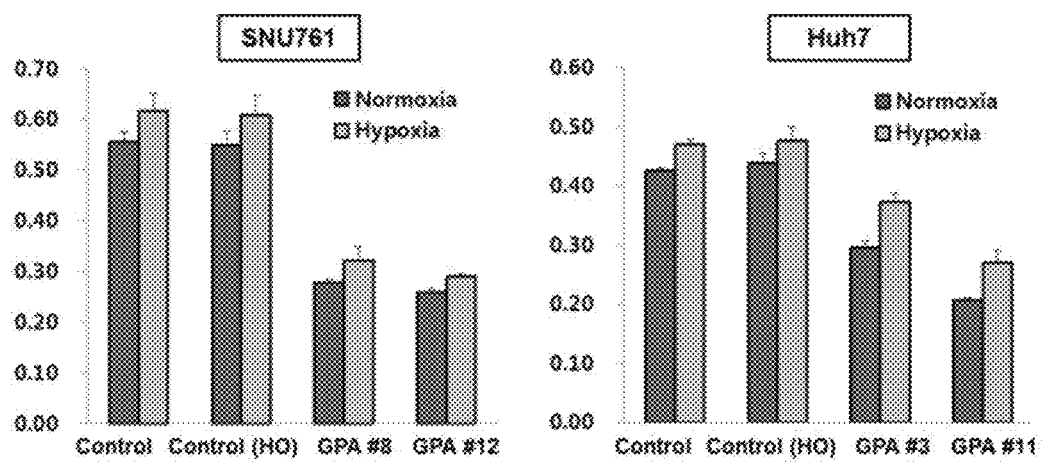
FIG. 6a and FIG. 6b are results of verifying an efficacy of inhibiting proliferation of a hepatocellular carcinoma cell of GPC3 aptamer discovered after primary or secondary SELEX respectively in vitro.

2.2 Evaluation of Efficacy of Inhibiting Proliferation of Hepatocellular Carcinomas of GPC3 Aptamers Using MTS Assay An efficacy of inhibiting proliferation of hepatocellular carcinomas of GPC3 aptamers was verified using a cell viability assay, MTS assay. As a result of MTS test, GPA #8 and #12 were administered to SNU61 and GPA #3 and #1 were administered to Huh7 among GPC3 aptamers discovered in the above Example 1 after the primary SELEX, and the result was shown in FIG. 6a. As a result, it was confirmed that the hepatocellular carcinoma cell growth was significantly inhibited in both SNU-761 and Huh-7, compared to groups where control or control(HO) was administered.

Figure 6B:
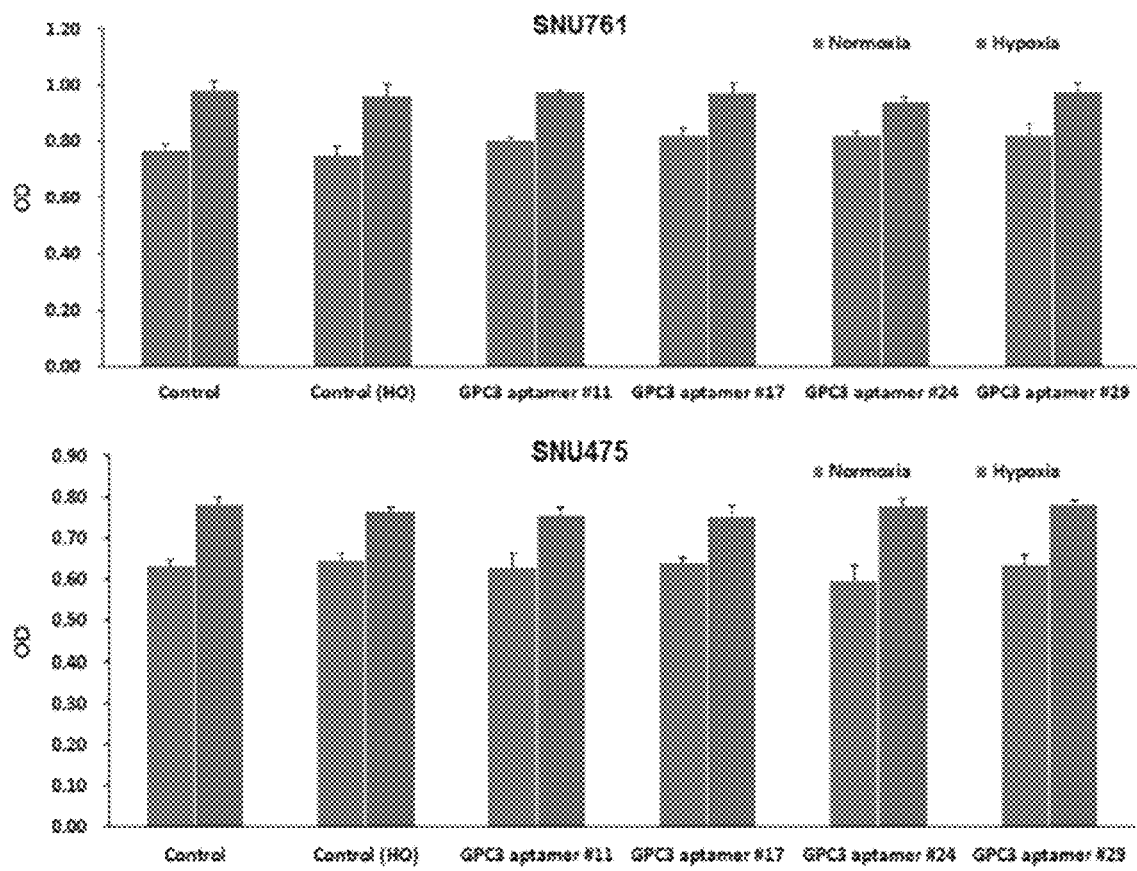

The result of cell growth as to GPC3 aptamers discovered in the secondary SELEX was shown in FIG. 6b, and it was confirmed that the GPC3 aptamers discovered in the secondary SELESx have superiorly high binding activity to the hepatocellular carcinoma cell lines compared to GPC3 aptamers discovered in the primary SELEX rather than hepatocellular carcinoma proliferation inhibition effect, and therefore, it was expected to be very high availability as a use of diagnosis such as early diagnosis of hepatocellular carcinomas.

Example 3. Mechanism of Glypican-3 (GPC3) Specific Binding Aptamer

After treating 2 kinds of GPC3 aptamers (SEQ ID NOs: 3 and 11) that their efficacy of inhibiting proliferation of hepatocellular carcinomas was confirmed to a hepatocellular carcinoma cell line, a signaling route related to proliferation and apoptosis of hepatocellular carcinoma cells, etc. was confirmed using immunoblotting. The result was shown in FIG. 8, and it was confirmed that a signal involving in cell survival and proliferation processes, erk1/2 expression was decreased after treatment of GPC3 aptamers, but it was confirmed that a caspase route inducing apoptosis was not activated. Therefore, it was expected that GPC3 aptamers would show an effect on inhibition of proliferation rather than direct induction of hepatocellular carcinoma cell death.

In addition, the result of confirming expression of Yap protein which was known as an intracellular downstream signal of a hepatocellular carcinoma specific membrane protein where GPC3 aptamers bind to using immunoblotting was shown in FIG. 9, and it was confirmed that expression of phosphorylated Yap was increased by GPC3 aptamer treatment.

The YAP is a kind of oncogenes, and it is known that if phosphorylated, mostly it cannot function any more as degraded. In other words, it can be seen that YAP was inactivated through GPC3 aptamers (phosphorylated YAP), and it inhibited growth of hepatocellular carcinoma cells. The mechanism was schematically shown in FIG. 10.

Example 4. Evaluation of Mouse Hepatocellular Carcinomas Tissues Selective Binding of GPC3 Aptamers Using PET Images In order to determine whether GPC3 aptamer selectively binds in pathological tissues, in vivo experiment was performed on GPC3 aptamer (SEQ ID NO: 39). After administering GPC3 aptamer and control aptamer into blood vessels to HCC xenograft disease model animals that were established by inoculation of the hepatocellular carcinoma cell line SNU-475 to nude mice (BALB/c nude mouse), it was observed whether it selectively binds to the hepatocellular carcinoma tissues.

Figure 7:
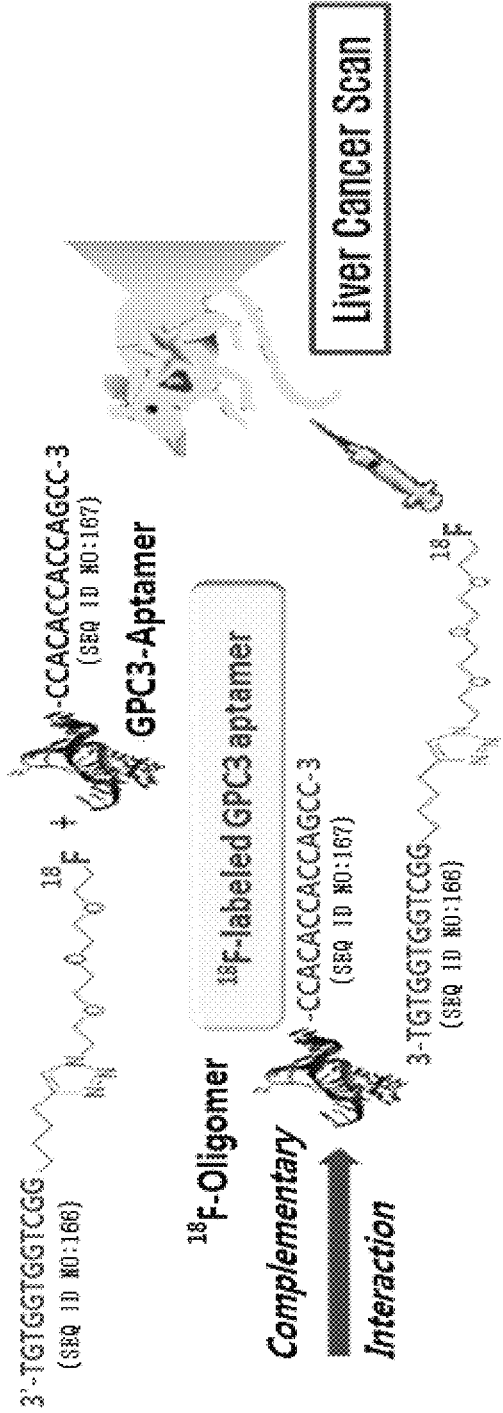
FIG. 7 is a schematic diagram of the diagnostic imaging method for hepatocellular carcinoma using GPC3 aptamer.

After SNU-475 tumor cells were injected into thighs of all mice at 1×10^5/mL and tumor sprouts were obtained, they were observed until tumor size was 0.2 cm³ for 7-10 days. Then, if confirmed that tumor was formed visually, GPC3 aptamer 558 uCi (1 nmole) labeled with F-18 Fluoride was injected through tail veins of nude mice, and imagess were obtained in 20 minutes, 60 minutes, and 120 minutes after injection (Inveon PET camera, Siemens). The process was schematized in FIG. 7, and the images obtained as a result were shown in FIG. 11.

As the result of experiment, in PET images of administering F-18 labeled GPC3 aptamer, tumor was observed in the thigh of nude mouse in the 20-min image. It was confirmed that in the early stage (20-min image), GPC3 aptamer was non-specifically distributed throughout the whole organs, but GPC3 aptamers binding tumor were increased as time went from 20 minutes to 60 minutes, and particularly GPC3 aptamer was still bound to tumor even after 120 minutes went. However, in case of the control aptamer, binding of aptamer in a tumor site was not observed not only after 20 minutes but also after 120 minutes.

Example 5. Evaluation of Hepatocellular Carcinoma Selective Binding of GPC3 Aptamer On the day before the experiment, 1×10^5 of hepatocellular carcinoma cell line SNU-475 or CHO (Chinese hamster ovary) as a control cell line was seeded. Cy5 labeled GPC3 aptamers were prepared by annealing GPC3 aptamers and Cy5-Anti-primers for 10 minutes. After washing seeded cells, Tris buffer (pH7.4) 500 µL and 500 pmole of Cy5 labeled GPC3 aptamers were added, and incubated at 4° C. for 30 minutes. After incubation, they were washed twice with PBS, and confocal image capture was performed with 4% formalin fixation (400-fold magnification). The binding of Cy5-Anti-primer and GPC3 aptamer was confirmed through agarose gel loading (FIG. 12).

It was observed that GPC3 aptamer had selective binding to the hepatocellular carcinoma SNU-475 on the confocal image, and it was confirmed that it did not bind to the hepatocellular carcinoma cell line in case of treating antiprimer only (FIG. 13a and FIG. 13b). It was confirmed that it did not bind to the control cell line CHO (Chinese hamster ovary) in both cases of treatment of GPC3 aptamer and anti-primer only (FIG. 14a and FIG. 14b).

Example 6. Mouse Biodistribution Study of GPC3 Aptamer

In order to determine mouse biodistribution of GPC3 aptamer, in vivo experiment was performed on GPC3 aptamers. HCC xenograft disease model animals were established by injecting the hepatocellular carcinoma cell line SNU-475 to the thigh of nude mice. 1000 pmole/100 µL/head of F-18 Fluoride labeled GPC3 aptamer was injected through tail veins of nude mice, and after one hour, mouse biodistribution was analyzed.

The result of analysis was shown in FIG. 15. Since in general, an aptamer is distributed little in digestion and excretion organs, not only GPC3 aptamers of the present invention were mostly distributed in the kidney, small intestine and large intestine, and next they were distributed in the major organs such as liver, lung, stomach, etc., but also GPC3 aptamers were partially remained in blood after 60 minutes. In particular, it was confirmed that the selective targeting effect of GPC3 aptamers to hepatocellular carcinoma tissues was significantly excellent, because larger amount of GPC3 aptamers were remained in the hepatocellular carcinoma tissue (SNU-475) produced in the thigh region than the normal muscle and femur.

---

The invention claimed is:

1. A Glypican-3 (GPC3) specific aptamer, specifically binding to a Glypican-3 protein and comprising deoxyuridine (dU) including a hydrophobic functional group substituted at 5-position of a pyrimidine group,
wherein the aptamer comprises a core sequence of one or more sequences selected from the group consisting of SEQ ID NO: 3, 8, 11, 12, 17, 24, 25, 29, and 39.

2. The aptamer of claim 1, wherein the hydrophobic functional group is a benzyl or a naphthyl group.

3. The aptamer of claim 1, further comprising one or more primer sequence selected from the group consisting of SEQ ID NO: 45 to SEQ ID NO: 48 to 5' end, 3' end or both ends of a core sequence.

4. The aptamer of claim 1, wherein the aptamer is characterized by being modified by further combining one or more selected from the group consisting of PEG (polyethylene glycol), idT (inverted deoxythymidine), LNA (Locked Nucleic Acid), 2'-methoxy nucleoside, 2'-amino nucleoside, 2'F-nucleoside, an amine linker, a thiol linker, and a cholesterol to 5' end, 3' end, or both ends of the aptamer.

5. The aptamer of claim 1, wherein the aptamer further comprises a radioactive isotope, a fluorescent molecule, a toxin or a control reagent.

6. A pharmaceutical composition for treating a hepatocellular carcinoma, preventing a hepatocellular carcinoma, or inhibiting hepatocellular carcinoma metastasis, comprising the aptamer of claim 1 as an active ingredient.

7. A Glypican-3 (GPC3) specific aptamer, specifically binding to a Glypican-3 protein and comprising deoxyuridine (dU) including a hydrophobic functional group substituted at 5-position of a pyrimidine group,
wherein the aptamer comprises a core sequence of one or more sequences selected from the group consisting of SEQ ID NO: 1, 2, 4 to 7, 9, 10, 13 to 16, 18 to 23, 26 to 28, 30 to 38, and 40 to 44.

8. The aptamer of claim 7, wherein the hydrophobic functional group is a benzyl or a naphthyl group.

9. The aptamer of claim 7, further comprising one or more primer sequence selected from the group consisting of SEQ ID NO: 45 to SEQ ID NO: 48 to 5' end, 3' end or both ends of a core sequence.

10. The aptamer of claim 7, wherein the aptamer is characterized by being modified by further combining one or more selected from the group consisting of PEG (polyethylene glycol), idT (inverted deoxythymidine), LNA (Locked Nucleic Acid), 2'-methoxy nucleoside, 2'-amino nucleoside, 2'F-nucleoside, an amine linker, a thiol linker, and a cholesterol to 5' end, 3' end, or both ends of the aptamer.

11. The aptamer of claim 7, wherein the aptamer further comprises a radioactive isotope, a fluorescent molecule, a toxin or a control reagent.

* * * * *